(12) United States Patent
Tukel

(10) Patent No.: US 9,814,756 B2
(45) Date of Patent: Nov. 14, 2017

(54) USE OF ISOLATED BACTERIAL AMYLOIDS FOR TREATMENT OF INFLAMMATORY DISORDERS OR DISEASES OF THE EPITHELIUM

(71) Applicant: TEMPLE UNIVERSITY—OF THE COMMONWEALTH SYSTEM OF HIGHER EDUCATION, Philadelphia, PA (US)

(72) Inventor: Cagla Tukel, Philadelphia, PA (US)

(73) Assignee: TEMPLE UNIVERSITY—OF THE COMMONWEALTH SYSTEM OF HIGHER EDUCATION, Philadelphia, PA (US)

(*) Notice: Subject to any disclaimer, the term of this patent is extended or adjusted under 35 U.S.C. 154(b) by 217 days.

(21) Appl. No.: 14/407,568

(22) PCT Filed: Jun. 12, 2013

(86) PCT No.: PCT/US2013/045397
§ 371 (c)(1),
(2) Date: Dec. 12, 2014

(87) PCT Pub. No.: WO2013/188529
PCT Pub. Date: Dec. 19, 2013

(65) Prior Publication Data
US 2015/0190463 A1 Jul. 9, 2015

Related U.S. Application Data

(60) Provisional application No. 61/660,087, filed on Jun. 15, 2012.

(51) Int. Cl.
| | | |
|---|---|---|
| *A61K 38/16* | (2006.01) | |
| *A61K 39/02* | (2006.01) | |
| *A61K 39/09* | (2006.01) | |
| *A61K 38/17* | (2006.01) | |

(52) U.S. Cl.
CPC ........ *A61K 38/164* (2013.01); *A61K 38/1716* (2013.01); *A61K 39/025* (2013.01); *A61K 39/09* (2013.01)

(58) Field of Classification Search
None
See application file for complete search history.

(56) References Cited

U.S. PATENT DOCUMENTS

| | | |
|---|---|---|
| 4,782,014 A | 11/1988 | Serban et al. |
| 7,998,474 B2 | 8/2011 | Kelly |
| 2004/0062757 A1 | 4/2004 | Finegold |
| 2006/0088910 A1 | 4/2006 | Nguyen |
| 2006/0127381 A1 | 6/2006 | Cui |
| 2007/0258953 A1 | 11/2007 | Duncan et al. |
| 2008/0044356 A1 | 2/2008 | Lesne et al. |
| 2009/0252708 A1 | 10/2009 | Fitzpatrick et al. |
| 2010/0129386 A1 | 5/2010 | Elson et al. |
| 2011/0251156 A1 | 10/2011 | Shen et al. |
| 2011/0269165 A1 | 11/2011 | Tsuji et al. |
| 2012/0039924 A1 | 2/2012 | Hershberg et al. |

FOREIGN PATENT DOCUMENTS

| | | |
|---|---|---|
| EP | 1481681 A1 | 1/2004 |
| EP | 2368564 A1 | 9/2011 |
| WO | 2005/030230 A1 | 4/2005 |
| WO | 2011/014693 A2 | 2/2011 |
| WO | 2011/051760 A1 | 5/2011 |
| WO | 2011/086172 A1 | 7/2011 |
| WO | 2011/159880 A1 | 12/2011 |
| WO | 2012/011100 A1 | 1/2012 |
| WO | 2012/039615 A2 | 3/2012 |

OTHER PUBLICATIONS

Oppong, G.O., et al "Biofilm-associated bacterial amyloids dampen inflammation in the gut: oral treatment with curli fibres reduces the severity of hapten-induced colitis in mice" npj Biofilms and Microbiomes, Oct. 14, 2015, 1,15019, p. 1-7 doi:10.1038/npjbiofilms.2015.19.*
Larson et al, Human Serum Amyloid A3 Peptide Enhances Intestinal MUC3 Expression and Inhibits EPEC Adherence, Biochemical and Biophysical Research Communication 300, pp. 531-540 (2003).
Tukel et al, Responses to Amyloids of Microbial and Host Origin are Mediated Through Toll-Like Receptor 2, Cell Host and Microbe 6, pp. 45-53 (Jul. 23, 2009).
Tukel et al, Toll-Like Receptors 1 and 2 Cooperatively Mediaste Immune Responses to Curli, a Common Amyloid from Enterobacterial Biofilms, Cellular Microbiology 12(10), pp. 1495-1505 (2010).
Otzen, Daniel, Functional Amyloid, Prion 4:4, pp. 256-264 (2010).
Chung et al, Microbiota-Stimulated Immune Mechanisms to Maintain Gut Homeostasis, Current Opinion in Immunology, 22(4), pp. 455-460 (2010).
Wang et al, The Molecular Basis of Functional Bacterial Amyloid Polymerization and Nucleation, Journal of Biological Chemistry, 283(31), pp. 21530-21539 (2008).

(Continued)

*Primary Examiner* — Chris R Tate
*Assistant Examiner* — Aaron J Kosar
(74) *Attorney, Agent, or Firm* — Drinker Biddle & Reath LLP

(57) ABSTRACT

A method for treatment of a subject having an inflammatory disease of the epithelium comprising the step of administering an amount of a composition comprising an isolated bacterial amyloid peptide to said subject. In embodiments, the composition is membrane-free. In embodiments, the composition comprises a curli fibril. In yet further embodiments, the isolated bacterial amyloid peptide is a CsgA polypeptide, a CsgA polypeptide fragment, a CsgB polypeptide or a CsgB polypeptide fragment. Also provided is a method for decreasing epithelium permeability in a tissue of a subject comprising epithelium comprising the step of administering an amount of a composition comprising an isolated bacterial amyloid peptide to the epithelium of the subject. In embodiments, the composition is membrane-free. In further embodiments, the composition comprises a curli fibril. In embodiments, the isolated bacterial amyloid peptide is a CsgA polypeptide, a CsgA polypeptide fragment, a CsgB polypeptide or a CsgB polypeptide fragment.

16 Claims, 19 Drawing Sheets

(56) References Cited

OTHER PUBLICATIONS

Otzen et al, Functional Bacterial Amyloid, Cellular and Molecular Life Sciences, 65(6), pp. 910-927 (2008).
Tukel et al, CsgA is a Pathogen-Associated Molecular Pattern of *Salmonella enterica* Serotype Typhimurium that is Recognized by Toll-Like Receptor 2" Molecular Microbiology 58, pp. 289-304, (2005).
Cario et al, Toll-Like Receptor 2 Controls Mucosal Inflammation by Regulating Epithelial Barrier Function, Gastroenterology 132, pp. 1359-1374, (2007).
International Search Report for PCT/US13/45397 dated Nov. 1, 2013.
Hammar, et al., Nucleator-Dependent Intercellular Assembly of Adhesive Curli Organelles in *Escherichia coli*, Proc. Natl. Acad. Sci. USA, vol. 93, pp. 6562-6566, (Jun. 1996).
Nenninger, et al., Localized and Efficient Curli Nucleation Requires the Chaperone-Like Amyloid Assembly Protein CsgF; PNAS, vol. 106, No. 3, pp. 900-905, (Jan. 2009).

* cited by examiner

SEQUENCE LISTING

```
<160> NUMBER OF SEQ ID NOS: 9

<210> SEQ ID NO 1
<211> LENGTH: 151
<212> TYPE: PRT
<213> ORGANISM: Escherichia coli

<400> SEQUENCE: 1

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
        50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150

<210> SEQ ID NO 2
<211> LENGTH: 151
<212> TYPE: PRT
<213> ORGANISM: Escherichia coli

<400> SEQUENCE: 2

Met Lys Asn Lys Leu Leu Phe Met Met Leu Thr Ile Leu Gly Ala Pro
1               5                   10                  15

Gly Ile Ala Ala Ala Ala Gly Tyr Asp Leu Ala Asn Ser Glu Tyr Asn
                20                  25                  30

Phe Ala Val Asn Glu Leu Ser Lys Ser Ser Phe Asn Gln Ala Ala Ile
            35                  40                  45

Ile Gly Gln Ala Gly Thr Asn Asn Ser Ala Gln Leu Arg Gln Gly Gly
        50                  55                  60

Ser Lys Leu Leu Ala Val Val Ala Gln Glu Gly Ser Ser Asn Arg Ala
65                  70                  75                  80
```

Lys Ile Asp Gln Thr Gly Asp Tyr Asn Leu Ala Tyr Ile Asp Gln Ala
                85                  90                  95

Gly Ser Ala Asn Asp Ala Ser Ile Ser Gln Gly Ala Tyr Gly Asn Thr
            100                 105                 110

Ala Met Ile Ile Gln Lys Gly Ser Gly Asn Lys Ala Asn Ile Thr Gln
        115                 120                 125

Tyr Gly Thr Gln Lys Thr Ala Ile Val Val Gln Arg Gln Ser Gln Met
    130                 135                 140

Ala Ile Arg Val Thr Gln Arg
145                 150

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized

<400> SEQUENCE: 3
tccatgacgt tcctgacgtt                                          20

<210> SEQ ID NO 4
<211> LENGTH: 20
<212> TYPE: DNA
<213> ORGANISM: Artificial Sequence
<220> FEATURE:
<223> OTHER INFORMATION: Chemically synthesized

<400> SEQUENCE: 4
tccatgacgt tcctgacgtt                                          20

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5
ctatacacca agttgtcagc                                          20

<210> SEQ ID NO 6
<211> LENGTH: 20
<212> TYPE: DNA
<213> ORGANISM: Artificial Sequence
<220> FEATURE:
<223> OTHER INFORMATION: Chemically synthesized

<400> SEQUENCE: 6
gtctccaact cagtaacctg                                          20

<210> SEQ ID NO 7
<211> LENGTH: 21
<212> TYPE: DNA
<213> ORGANISM: Artificial Sequence
<220> FEATURE:
<223> OTHER INFORMATION: Chemically synthesized

<400> SEQUENCE: 7
gccaaagtct tgattgattg g                                        21

<210> SEQ ID NO 8
<211> LENGTH: 20

```
<212> TYPE: DNA
<213> ORGANISM: Artificial Sequence
<220> FEATURE:
<223> OTHER INFORMATION: Chemically synthesized

<400> SEQUENCE: 8
ttgaagttct ccagctcctg                                                 20

<210> SEQ ID NO 9
<211> LENGTH: 41
<212> TYPE: PRT
<213> ORGANISM: Escherichia coli

<400> SEQUENCE: 9

Ser Asp Ile Thr Val Gly Gln Tyr Gly Gly Asn Asn Ala Ala Leu Val
1               5                   10                  15

Asn Gln Thr Ala Ser Asp Ser Ser Val Met Val Arg Gln Val Gly Phe
                20                  25                  30

Gly Asn Asn Ala Pro Ala Asn Gln Tyr
            35                  40
```

USE OF ISOLATED BACTERIAL AMYLOIDS FOR TREATMENT OF INFLAMMATORY DISORDERS OR DISEASES OF THE EPITHELIUM

CROSS-REFERENCE TO RELATED APPLICATION

The benefit of the filing date of U.S. Provisional Patent Application No. 61/660,087, filed Jun. 15, 2012, is hereby claimed. The entire disclosure of the aforesaid application is incorporated herein by reference.

REFERENCE TO GOVERNMENT GRANT

The invention was made with government support under grant no. U54AI57168 awarded by the National Institutes of Health. The government has certain rights in this invention.

FIELD OF THE INVENTION

The invention relates to the use of isolated bacterial amyloids or the use of recombinant bacteria for the treatment of inflammatory disorders of the epithelium.

SEQUENCE LISTING

The instant application contains a Sequence Listing which has been submitted in ASCII format via EFS-Web and is hereby incorporated by reference in its entirety. Said ASCII copy, created on Jun. 11, 2013, is named 35926_0457_00_WO_SeqListing_ST25, and is 4,700 bytes in size.

BACKGROUND OF THE INVENTION

The intestinal epithelium represents a physical as well as an immunologic barrier, which is in constant contact with approximately $10^{13}$-$10^{14}$ microorganisms. (Gill S R, Pop M, Deboy R T, Eckburg P B, Turnbaugh P J, Samual B S, Gordon J I, Reiman D A, Fraser-Liggett and Nelson K E, 2006. Metagenomic analysis of the human distal gut microbiome. *Science* 312:1355-1359; Turnbaugh P J, Ley R E, Hamady M, Fraser-Liggett C M, Knight R, and Gordon J I, 2007. The human microbiome project. *Nature* 449:804-810; Xu J and Gordon J I, 2003. Inaugural Article: Honor thy symbionts. *Proc Natl Acad Sci USA* 100:10452-10459). Bacteria comprise the vast majority of the intestinal organisms with at least 1000 different species present within the community (Hooper L V, 2009. Do symbiotic bacteria subvert host immunity? *Nat Rev Microbiol* 7:367-374; Qin J, Li R, Raes J et al. 2010. A human gut microbial gene catalogue established by metagenomic sequencing. *Nature* 464:59-65; Zang T, Breitbart M, Lee W H, Run J Q, Wei C L, Soh S W, Hibberd M L, Liu E T, Rohwer F and Ruan Y, 2006. RNA viral community in human feces: prevalence of plant pathogenic viruses. *PLoS Biol* 4:e3). Therefore, there is a critical need for mechanisms through which the host is protected from hyper-responsive inflammatory processes due to the presence of an unprecedented amount of antigens while still supporting the growth of commensal bacteria which are beneficial to host health and function.

As a first line of innate immune response, the intestinal epithelium has been found to play an important role in the maintenance and regulation of gastrointestinal homeostasis. For instance, it is currently known that the production of antimicrobial peptides and lectins by enterocytes and Paneth cells (Ayabe T, Satchell D P, Wilson C L, Parks W C, Selsted M E and Ouellette A J, 2000. Secretion of microbicidal alpha-defensins by intestinal Paneth cells in response to bacteria. *Nat Immunol* 1:113-118; Cash H L, Whitham C V, Behrendt C L and Hooper L V, 2006. Symbiotic bacteria direct expression of an intestinal bactericidal lectin. *Science* 313:1126-1130; Christa L, Carnot F, Simon M T, Levavasseur F, Stinnakre M G, Lasserre C, Thepot D, Clement B, Devinoy E, and Brechot C, 1996. HIP/PAP is an adhesive protein expressed in hepatocarcinoma, normal Paneth, and pancreatic cells. *Am J Physiol* 271:G993-1002; Cunliffe R N, Rose F R, Keyte J, Abberley L, Chan W C, and Mahida Y R, 2001. Human defensin 5 is stored in precursor form in normal Paneth cells and is expressed by some villous epithelial cells and by metaplastic Paneth cells in the colon in inflammatory bowel disease. *Gut* 48:176-185; Satchell D P, Sheynis T, Shirafuji Y, Kolusheva S, Ouellette A J, and Jelinek R, 2003. Interactions of mouse Paneth cell alpha-defensins and alpha-defensin precursors with membranes. Prosegment inhibition of peptide association with biomimetic membranes. Prosegment inhibition of peptide associations with biomimetic membranes. *J Biol Chem* 278:13838-13846), the production of mucins by goblet cells (Bergstrom K S, Kissoon-Singh V, Gibson D L, Ma C, Montero M, Sham H P, Ryz N, Huang T, Velcich A, Finlay B B, Chadee K and Valiance B A, 2010. Muc2 protects against lethal infectious colitis by disassociating pathogenic and commensal bacteria from the colonic mucosa. *PLoS Pathog* 6:e1000902; Van der Sluis M, De Koning B A, et al. 2006. Muc2-deficient mice spontaneously develop colitis, indicating that MUC2 is critical for colonic protection. *Gastroenterology* 131:117-129) and modulation of epithelial barrier integrity all act in concert to regulate and maintain intestinal immune homeostasis (Rakoff-Nahoum, S., Paglino J, Eslami-Varzaneh F, Edgerg S, and Medzhitov R, 2004. Recognition of commensal microflora by toll-like receptors is required for intestinal homeostasis. *Cell* 118:229-241).

Toll-like receptors (TLRs) comprise a family of innate pattern recognition receptors (PRRs) that sense conserved microbial structures known as pathogen-associated molecular patterns (PAMPs) and endogenous danger molecules (Akira S and Takeda K, 2004. Toll-like receptor signaling. *Nat Rev Immunol* 4:499-511; Medzhitov R, 2007. Recognition of microorganisms and activation of the immune response. *Nature* 449:819-826; Takeda K, and Akira S, 2007. Toll-like receptors. *Curr Protoc Immunol* Chapter 14: Unit 14 12). TLR2, a member of this family, recognizes a number of conserved molecular patterns including lipopeptides, lipoteichoic acid and zymosan, through the formation of heterodimers with TLR1 or with TLR6 (Aliprantis A O, Yang R B, Mark M R, Suggett S, Devaux B, Radolf J D, Klimpel G R, Godowski P and Zychlinsky A, 1999. Cell activation and apoptosis by bacterial lipoproteins through toll-like receptor-2. *Science* 285:736-739; Brightbill H D, Libraty D H, Krutzik S R, Yang R B, Belisle J T, Bleharski J R, et al. 1999. Host defense mechanisms triggered by microbial lipoproteins through toll-like receptors. *Science* 285:732-736; Takeda K and Akira S, 2004. TLR signaling pathways. *Semin Immunol* 16:3-9; Takeuchi O, Hoshino K, Kawai T, Sanjo H, Takada H, Ogawa T, Takeda K, and Akira S, 1999. Differential roles of TRL2 and TLR4 in recognition of gramm-negative and gram-positive bacterial cell wall components. *Immunity* 11:443-451; Takeuchi O, Kawai T, Muhlradt P F, Morr M, Radolf J D, Zychlinsky A, Takeda K and Akira S, 2001. Discrimination of bacterial lipoproteins by Toll-like receptor 6. *Int Immunol* 13:933-940; Takeuchi 0, Sato S, Horiuchi T, Hoshino K, Takeda K, Dong Z, Modlin R L and Akira S, 2002. Cutting edge: role of Toll-like receptor 1 in mediating immune response to microbial lipoproteins. *J Immunol* 169:10-14). MyD88 (myeloid differentiation primary response gene 88) and Mal/TIRAP are both required for TLR2 dependent signaling where nuclear factor-kappa B (NF-kB) is activated. While Mal/TIRAP is involved in bridging MyD88 to the TLR2 receptor complex and directing the recruitment of TRAF6 which is necessary for NF-kB activation, Mal binds to the p85α subunit of phosphatidylinositol 3-kinase (PI3K) upon activation of TLR2/TLR6 heterodimer resulting in Akt phosphorylation which consequently leads to macrophage polarization, and cell survival by inhibiting apoptosis. In contrast, TLR2/TLR1 mediated activation of PI3K occurs in the absence of Mal and MyD88 suggesting the presence of another adaptor molecule (Franke T F, Kaplan D R, and Cantley L C, 1997. PI3K:downstream AKTion blocks apoptosis. *Cell* 88:435-437; Mansell A, Brint E, Gould J A, O'Neill La and Hertzog P J, 2004. Mal interacts with tumor necrosis factor receptor-associated factor (TRAF)-6 to mediate NF-kappaB activation by toll-like receptor (TLR)-2 and TLR4. *J Biol Chem* 279:37227-37230; Santos-Wierra S et al., 2009. Mal connects TLR2 to PI3 Kinase activation and phagocyte polarization. *EMBO J* 28:2018-2027). Activation of PI3K pathway as a downstream effect of TLR2 activation has also been shown to augment the tight junction-associated epithelial barrier integrity possibly by acting as a surveillance receptor, which monitors luminal bacteria and translocation of pathogens (Cario E, Gerken G and Podolsky D K, 2007. Toll-like receptor 2 controls mucosal inflammation by regulating epithelial barrier function. *Gastroenterology* 132: 1359-1374; Cario E, Gerken G and Podolsky D K, 2004. Toll-like receptor 2 enhances ZO-1 associated intestinal epithelial barrier integrity via protein kinase C. *Gastroenterology* 127:224-238; Podolsky D K, Gerken G, Eyking A and Cario E, 2009. Colitis-associated variant of TLR2 causes impaired mucosal repair because of TFF3 deficiency. *Gastroenterology* 137:209-220).

Amyloids

Amyloids that possess a fibrillar cross-β sheet quaternary structure are produced both by humans and bacteria. While amyloids in humans are mostly associated with complex diseases, functional amyloids that serve a role in physiological processes such as melanin production and blood clotting have been reported (Aigelsreiter A et al. 2007. How a cell deals with abnormal proteins. Pathogenic mechanisms in protein aggregation diseases. *Pathobiology* 74:145-158; Brandan E and Inestrosa N C, 1993. Extracellular matrix components and amyloid in neuritic plaques of Alzheimer's disease. *Gen Pharmacol* 24:1063-1068; Hull R L et al., 2004. Islet amyloid: a critical entity in the pathogenesis of type 2 diabetes. *J Clin Endocrinol Metab* 89:3629-3643; Leonhardt R M et al. Endoplasmic reticulum export, subcellular distribution, and fibril formation by Pmel17 require an intact N-terminal domain junction. *J Biol Chem* 285: 16166-16183; Pfefferkorn C M, McGlinchey R P and Lee J C, 2010. Effects of pH on aggregation kinetics of the repeat domain of a functional amyloid, Pmel17. *Proc Natl Acad Sci USA* 107:21447-21452; Theos et al., 2005. The Silver locus product Pmel17/gp100/Silv/ME20: controversial in name and in function. *Pigment Cell Res* 18:322-336).

In bacteria, amyloids function as a component of the extracellular matrix in biofilms of commensal organisms such as spore forming *Bacillus subtilis*, *Pseudomonas fluorescens* or human pathogens such as *Mycobacterium tuberculosis*, *Salmonella enterica* serovar *Typhimurium*, *Citrobacter freundii*, *Enterobacter sakazakii* and *Escherichia coli* (Alteri et al., 2007. *Mycobacterium tuberculosis* produces pili during human infection. *Proc Natl Acad Sci USA* 104: 5145-5150; Blanco L P et al., 2011. Diversity, biogenesis and function of microbial amyloids. *Trends Microbiol* 20:66-73; Chapman M R et al. 2002. Role of *Escherichia coli* curli operons in directing amyloid fiber formation. *Science* 295:851-855; Collinson S K et al, 1996. *Salmonella enteritidis* agfBAC operon encoding thin, aggregative fimbriae. *J Bacteriol* 178:662-667; Dueholm M S, et al. 2010. Functional amyloid in *Pseudomonas*. *Mol. Microbiol* 77(4): 1009-1020; Larsen P et al., 2007 Amyloid adhesins are abundant in natural biofilms. *Environ Microbiol* 9:3077-3090; Romero C et al, 2010. Amyloid fibers provide structural integrity to *Bacilus subtilis* biofilms. *Proc Natl Acad Sci USA* 107:2230-2234; Zogaj X et al. 2003. Production of cellulose and curli fimbriae by members of the family Enterobacteriaceae isolated from the human gastrointestinal tract. *Infect Immun* 71:4151-4158).

Curli fibrils produced by enteric bacteria including *Salmonella* spp and *E. coli* are the best-characterized bacterial amyloid to date. Earlier studies have shown that curli fibrils activate the immune system inducing the production of inflammatory cytokines in a mouse model of sepsis as well as urinary tract infection induced by *E. coli* (Bian Z, Brauner A, Li Y and Normark S, 2000. Expression of and cytokine activation by *Escherichia coli* curli fibers in human sepsis. *J Infect Dis* 181:602-612; Bian Z, Yan Z Q, Hansson G K, Thoren P and Normark S, 2001. Activation of inducible nitric oxide synthase/nitric oxide by curli fibers leads to a fall in blood pressure during systemic *Escherichia coli* infection in mice. *J Infect Dis* 183:612-619; Kai-Larsen Y et al. 2010. Uropathogenic *Escherichia coli* modulates immune responses and its curli fimbriae interact with the antimicrobial peptide LL-37. *PLoS Pathog* 6:e1001010; Tukel C et al, 2010. Toll-like receptors 1 and 2 cooperatively mediate immune responses to curli, a common amyloid from enterobacterial biofilms. *Cell Microbiol* 12:1495-1505; Tukel C et al., 2005. CsgA is a pathogen-associated molecular pattern of *Salmonella enterica* serotype *Typhimurium* that is recognized by Toll-like receptor 2. *Mol Microbiol* 58:289-304; Tukel C et al. 2009. Responses to amyloids of microbial and host origin are mediated through Toll-like receptor 2. *Cell Host and Microbe* 6(1):45-53).

Curli fibrils are indeed a pathogen-associated molecular pattern (PAMP) that is recognized by the TLR2/1 heterodimer. Interestingly, TLR2 responds not only to curli fibrils but also recognizes host amyloids such as β-amyloid 1-40 and β-amyloid 1-42 of Alzheimer's plaques as well as serum amyloid A, an acute phase protein (Cheng et al., 2008. Cutting edge: TLR2 is a functional receptor for acute-phase serum amyloid A. *J Immunol* 181:22-26; He R L et al. 2009. Serum amyloid A induces a G-CSF expression and neutrophilia via Toll-like receptor 2. *Blood* 113:429-437; Jana M et al. 2008. Fibrillar amyloid-beta peptides activate microglia via TLR2: implications for Alzheimer's disease. *J Immunol* 181:7254-7262; Reed-Geaghan E G et al. 2009CD14 and toll-like receptors 2 and 4 are required for fibrillar a{beta}-stimulated microglial activation. *J Neurosci* 29:11982-11992; Tukel C et al, 2010. Toll-like receptors 1 and 2 cooperatively mediate immune responses to curli, a common amyloid from enterobacterial biofilms. *Cell Microbiol* 12:1495-1505; Udan M L et al. 2008. Toll-like receptors 2 and 4 mediate Abeta(1-42) activation of the innate immune response in a human monocytic cell line. *J Neurochem.* 104(2):524-533). In fact, TLR2 recognizes the conserved quaternary β-sheet structure that is common to amyloids of all distinct origins.

Amyloids have also been reported to be present in the biofilms of members of Bacteriodetes and Firmicutes, the predominant phyla found in the gastrointestinal tract (Larsen P et al., 2007. Amyloid adhesins are abundant in natural biofilms. *Environ Microbiol* 9:3077-3090; Lay C et al., 2005. Design and validation of 16S rRNA probes to enumerate members of the *Clostridium leptum* subgroup in human faecal microbiota. *Environ Microbiol* 7:933-946).

Frequently, inflammatory disorders or diseases occur at or near an epithelium, such as that of the skin, the cornea or the gastrointestinal lining. Inflammatory disorders or diseases of the epithelium include the following.

Inflammatory Bowel Disease

Crohn's disease (CD) and ulcerative colitis (UC), and to a lesser extent, indeterminate colitis and infectious colitis, are collectively referred to as inflammatory bowel disease (IBD). Inflammatory bowel diseases are chronic recurrent inflammatory diseases of unclear etiology, affecting the small intestine and colon. IBD can involve either or both the small and large bowel. These disorders or diseases fall into the category of "idiopathic" IBD because the etiology for them is unknown.

Pathologic findings are generally not specific, although they may suggest a particular form of IBD. "Active" IBD is characterized by acute inflammation. "Chronic" IBD is characterized by architectural changes of crypt distortion and scarring. The term "crypt" refers to a deep pit that protrudes down into the connective tissue surrounding the small intestine. Crypt abscesses (active IBD characterized by the presence of neutrophils in crypt lumens) can occur in many forms of IBD, not just UC. Under normal conditions the epithelium at the base of the crypt is the site of stem cell proliferation and the differentiated cells move upwards and are shed 3-5 days later at the tips of the villi. This normal process, necessary for proper bowel function, is interrupted by IBD.

UC involves the colon as a diffuse mucosal disease with distal predominance. The rectum is virtually always involved, and additional portions of colon may be involved extending proximally from the rectum in a continuous pattern. Most often the UC occurs in young people 15 to 40 years of age. UC occurs only in the inner lining of the colon (large intestine) or rectum. When it is localized in the rectum, it is called "proctitis."

CD is a chronic inflammatory disease that has periods of remission (time when a person feels well) and relapse (when a person feels ill). CD is an inflammation and ulceration process that occurs in the deep layers of the intestinal wall. The most common areas affected are the lower part of the small intestine, called the ileum, and the first part of the colon. This type of CD is called ileocolitis. CD can infrequently affect any part of the upper gastrointestinal tract. Aphthous ulcers, which are similar to cold sores, are common. Ulcers can also occur in the esophagus, stomach and duodenum.

Therapy for IBD has historically included administration of corticosteroids. However, drawbacks of long term corticosteroid therapy include masking (or induction) of intestinal perforation, osteonecrosis and metabolic bone disease. Additional problems relate to development of corticosteroid dependency (Habnauer, *New England Journal of Medicine*, 334(13):841-848). Aminosalicylates such as sulfasalazine and mesalamine have been used to treat mild or moderately active UC and CD, and to maintain remission (Id at 843). Immunomodulatory drugs such as azathioprine and mercapto purine have been used in long term treatment for patients with IBD. Common complications with both of these drugs include pancreatitis, which occurs with an incidence of 3-15% of patients, and bone marrow suppression, which requires regular monitoring. More potent immunosuppressive drugs such as cyclosporine and methotrexate have been employed, but toxicity of these drugs limits their use to specific situations of refractory disease states. Other therapeutic approaches include antibiotic therapy and nutritional therapy. Often, therapy involves a combination of the above-described drug therapies in addition to surgical resection of the bowel.

There is no cure for IBD. Ultimately, the chronic and progressive nature of IBD demands a long-term treatment that maximizes the local anti-inflammatory effect while minimizing the global systemic effect on the immune system.

Chronic inflammatory disorders or diseases such as CD typically demonstrate periods of remission between intervals when the inflammatory is active and requires acute treatment. This is an example of a circumstance wherein it is known beforehand that an individual will develop, or is likely to develop an inflammatory disorder or disease.

Inflammatory Skin Disorders or Diseases

1. Psoriasis

Another chronic inflammatory condition of the epithelium is psoriasis. Psoriasis is a chronic, recurrent, papulosquamous plaque on areas of trauma such as the elbow, knee or scalp, though it may appear elsewhere on the skin. Psoriasis may coexist with *lupus erythematosis* in some individuals. Current treatments include topical administration of psoralens. "Psoralens" refers to a group of substances found in many different plants; especially psoralea corylifolia. Psoralens interact with nucleic acids and are also sued as research tools. Psoriasis is also treated by long-wave ultraviolet radiation. Neither treatment cures or prevents recurrence of psoriasis symptoms.

2. Atopic Dermatitis/Eczema

Atopic dermatitis is a chronic disease that affects the skin. In atopic dermatitis, the skin becomes extremely itchy. Scratching leads to redness, swelling, cracking, "weeping" clear fluid, and finally, crusting and scaling. In most cases, there are periods of exacerbations followed by periods of remissions. Although it is difficult to identify exactly how many people are affected by atopic dermatitis, an estimated 20% of infants and young children experience symptoms of the disease. Approximately 60% of these infants continue to have one or more symptoms of atopic dermatitis in adulthood. Thus, more than 15 million people in the United States have symptoms of the disease.

3. Contact Dermatitis

Contact dermatitis is a reaction that occurs when the skin comes into contact with an allergen, i.e., a substance to which the body is allergic. Allergens, though harmless to most individuals, cause an allergic reaction in individuals having a congenital or acquired hypersensitivity to the specific allergen.

Aphthous Ulcers (Oral)

Although the cause of aphthous ulcers remains unknown, many physicians believe they are caused by autoimmune phenomena, which cause the destruction of discrete areas of the oral mucosa which leads to oral ulceration. Among the cytokines present in these active areas of ulceration, TNF-α appears to play a predominant role.

Peptic Ulcer Disease

Inhibition of gastric acid secretion with $H_2$-receptor antagonists and, more recently, blockers of $H^+$, $K^+$-ATPase (also known as the proton pump) has been the mainstay of therapy for peptic ulcer disease. The pathophysiology of peptic ulcers remains obscure. An appreciation of the complexity of the physiology of the gastric mucosa has led to a hypothesis that peptic ulcers are the result of an imbalance in the relative importance of aggressive (acid, pepsin) and protective (mucus, bicarbonate, blood flow, prostaglandins, etc.) factors. Infection of the mucosa of the human gastric antrum with the bacterium *Helicobacter pylori* has been widely accepted as the cause of chronic, active, type B gastritis. Further, this form of gastritis has been linked directly to peptic ulcer disease by studies showing that eradication of *H. pylori* reverses this gastritis and prevents duodenal ulcer relapse.

There remains a need for a method of treating or preventing inflammatory disorders or diseases of the epithelium.

SUMMARY OF THE INVENTION

Provided is a method for the treatment of a subject having an inflammatory disease of the epithelium comprising the step of administering an effective amount of a composition comprising an isolated bacterial amyloid peptide to the subject. In some embodiments, the composition is membrane-free. In further embodiments, the composition comprises a curli fibril. In yet further embodiments, the isolated bacterial amyloid peptide is a CsgA polypeptide, a CsgA polypeptide fragment, a CsgB polypeptide or a CsgB polypeptide fragment.

In some embodiments, the inflammatory disease is inflammatory bowel disease or an inflammatory skin disease. In further embodiments, the inflammatory bowel disease is Crohn's disease or ulcerative colitis. In yet further embodiments, the inflammatory skin disease is psoriasis.

In some embodiments, the composition is administered orally, intracolonically or topically.

In some embodiments, the subject is a mammal. In further embodiments, the subject is a human.

In some embodiments the isolated bacterial amyloid peptide is complexed with DNA. In further embodiments, the DNA is of synthetic origin or non-synthetic orgin.

Also provided is a method for decreasing epithelium permeability in a tissue of a subject comprising epithelium comprising the step of administering an effective amount of a composition comprising an isolated bacterial amyloid peptide to the epithelium of the subject. In some embodiments, the composition is membrane-free. In further embodiments, the composition comprises a curli fibril. In yet further embodiments, the isolated bacterial amyloid peptide is a CsgA polypeptide, a CsgA polypeptide fragment, a CsgB polypeptide or a CsgB polypeptide fragment.

In some embodiments, the inflammatory disease is inflammatory bowel disease or an inflammatory skin disease. In further embodiments, the inflammatory bowel disease is Crohn's disease or ulcerative colitis. In yet further embodiments, the inflammatory skin disease is psoriasis.

In some embodiments, the composition is administered orally, intracolonically or topically.

In some embodiments, the subject is a mammal. In further embodiments, the subject is a human.

Also provided is a method for the treatment of a subject having an inflammatory disease of the epithelium comprising the step of administering to said subject an effective amount of a composition comprising a recombinant bacterium comprising a heterologous polynucleotide that encodes a heterologous bacterial amyloid peptide. In some embodiments, the composition comprises a curli fibril. In further embodiments, the bacterial amyloid peptide is a CsgA polypeptide, a CsgA polypeptide fragment, a CsgB polypeptide or a CsgB polypeptide fragment.

In some embodiments, the inflammatory disease is inflammatory bowel disease or an inflammatory skin disease. In further embodiments, the inflammatory bowel disease is Crohn's disease or ulcerative colitis. In yet further embodiments, the inflammatory skin disease is psoriasis.

In some embodiments, the composition is administered orally, intracolonically or topically.

In some embodiments, the subject is a mammal. In further embodiments, the subject is a human.

Also provided is a method for decreasing epithelium permeability in a tissue of a subject comprising epithelium comprising the step of administering an effective amount of a composition comprising a recombinant bacterium comprising a heterologous polynucleotide that encodes a heterologous bacterial amyloid peptide. In some embodiments, the composition comprises a curli fibril. In further embodiments, the bacterial amyloid peptide is a CsgA polypeptide, a CsgA polypeptide fragment, a CsgB polypeptide or a CsgB polypeptide fragment.

In some embodiments, the inflammatory disease is inflammatory bowel disease or an inflammatory skin disease. In further embodiments, the inflammatory bowel disease is Crohn's disease or ulcerative colitis. In yet further embodiments, the inflammatory skin disease is psoriasis.

In some embodiments, the composition is administered orally, intracolonically or topically.

In some embodiments, the subject is a mammal. In further embodiments, the subject is a human.

Provided is the use of an effective amount of a composition comprising an isolated bacterial amyloid peptide, for the treatment of a subject having an inflammatory disease of the epithelium.

Provided is the use of an effective amount of a composition comprising an isolated bacterial amyloid peptide, for decreasing epithelium permeability in a tissue of a subject comprising epithelium.

Provided is the use of an effective amount of a composition comprising a recombinant bacterium comprising a heterologous polynucleotide that encodes a heterologous bacterial amyloid peptide, for the treatment of a subject having an inflammatory disease of the epithelium.

Provided is the use of an effective amount of a composition comprising a recombinant bacterium comprising a heterologous polynucleotide that encodes a heterologous bacterial amyloid peptide, for decreasing epithelium permeability in a tissue of a subject comprising epithelium.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

BRIEF DESCRIPTION OF THE DRAWINGS

FIG. 1A also shows the expression of both TLR2 and TLR1 by RT-PCR on RNA extracted from T-84 cells.

DEFINITIONS

Figure 1A:
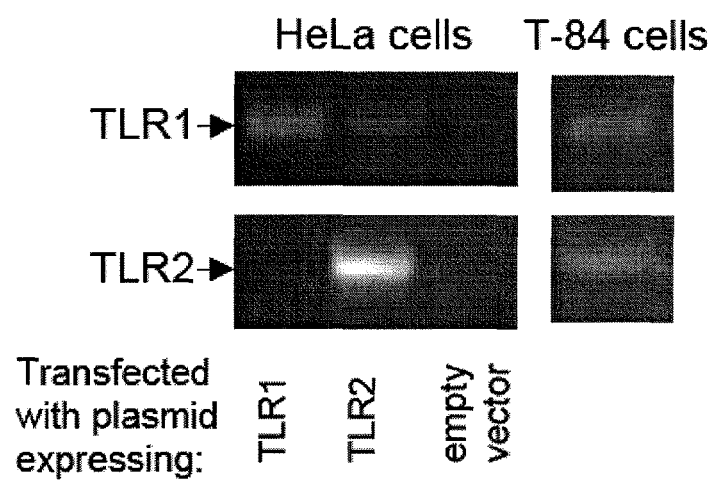
FIG. 1A illustrates the determination of the expression of TLR2 and TLR1 by RT-PCR on RNA extracted from Hela cells transfected with an empty vector, TLR2 (lane 2), TLR1 expression vector.

As used herein, each of the following terms has the meaning associated with it in this section.

The articles "a" and "an" are used herein to refer to one or to more than one (i.e. to at least one) of the grammatical object of the article. By way of example, "an element" means one element or more than one elements.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

As used herein with respect to formulations, the term "additional ingredients" includes, but is not limited to, one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, ed. Mack Publishing Co., 1985, Easton, Pa.), which is incorporated herein by reference.

"Applicator," as the term is used herein, is used to identify any device including, but not limited to, a hypodermic syringe, a pipette, and the like, for administering the peptides and compositions used in the practice of the invention.

"Container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., decreasing epithelial permeability in a subject.

The expression "effective amount", when used to describe therapy to an individual, refers to the amount of a compound that results in a therapeutically useful effect. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein the term "heterologous" with reference to a polynucleotide or protein refers to a polynucleotide or protein that does not naturally occur in a host cell. It is intended that the term encompass proteins that are encoded by naturally occurring genes, mutated genes, and/or synthetic genes.

The term "in vitro method," as used herein, refers to a method carried out outside of a living organism as opposed to an "in vivo method" which is a method carried out inside or on a living organism.

The term "inflammation" or "inflammatory response" refers to a defense reaction of living tissue to injury. The response serves to contain and to repair the injury. Multiple chemical mediators of inflammation derived from either plasma or cells have been observed. Compounds produced in the metabolism of arachidonic acid, such as prostaglandins and leukotrienes, also affect inflammation, leukotrienes mediating essentially every aspect of acute inflammation.

An "inflammatory disorder or disease of an epithelial tissue" or "of an epithelium" refers to an inflammatory disorder or disease in which one or more epithelial tissues or tissues adjacent to the epithelial layer are affected. Exemplary epithelial tissues include the epidermal layer of the skin, the cornea epithelium of the eye, and the epithelia associated with the mucosal linings of the respiratory, alimentary, gastrointestinal and urinary tracts.

"Pharmaceutically acceptable carrier" refers herein to a composition suitable for delivering an active pharmaceutical ingredient, such as a compound of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

As used herein the term "recombinant bacterium" means a bacterium comprising an expression vector or DNA construct comprising a heterologous polynucleotide encoding a heterologous bacterial amyloid protein according to the invention.

A "therapeutic" treatment is a treatment administered to a subject who exhibits signs of pathology of a disease or disorder for the purpose of diminishing or eliminating those signs.

The term "bacterial amyloid," as used herein refers to an amyloid of bacterial origin. Amyloids are aggregates of amyloid peptides/proteins possessing a fibrillar cross-β sheet quaternary structure and function in bacteria as a component of the extracellular matrix in biofilms of commensal organisms. Curli fibrils are the best-characterized bacterial amyloid. Curli expressed by *E. coli* as well as other members of the Enterobacteriaceae family, are found in enteric biofilms and facilitate the adherence of bacteria to biotic and abiotic surfaces. Curli are composed of two polypeptides of different amino acid sequences (CsgA and CsgB). However, many amyloids are composed of identical polypeptides.

Amyloid fibers have a characteristic morphology under electron microscopy, are β-sheet rich, typically non-branching, and react characteristically with certain amyloid-specific dyes such as thioflavin T (ThT) and Congo red. Bacteria that produce amyloid can be identified by Congo red staining (Nenninger et al., 2009. *Proc Natl Acad Sci USA* 106(3):900-905; Tukel C et al, 2010. *Cell Microbiol* 12:1495-1505; Hammar et al., 1996. *Proc Natl Acad Sci USA* 93:6562-6566). Briefly, in some embodiments, bacteria are grown on YESCA agar containing 20 mg/liter Congo Red (Sigma) and 10 mg/liter Coomassie brilliant blue G (Sigma).

In some embodiments, amyloid fibers are composed of one protein subunit, e.g., CsgA. In some embodiments, amyloid fibers are composed of two different protein subunits, e.g., CsgA and CsgB. In some embodiments, amyloid fibers are composed of more than two amyloid species. In some embodiments, amyloid fibers comprise CsgA and/or CsgB. The ratio of first polypeptide to second polypeptide in the fiber can vary. In some embodiments, the fiber is composed largely of the second amyloidogenic polypeptide. For example, in some embodiments the second polypeptide species constitutes at least 70%, at least 80%, at least 90%, or more of the fiber by weight, or, in some embodiments by number of subunits. In some embodiments, the first polypeptide species constitutes at least 70%, at least 80%, at least 90%, or more of the fiber by weight, or, in some embodiments by number of subunits. In one aspect, peptides that are derived from a first amyloidogenic polypeptide, and to which a second amyloidogenic polypeptide having a different sequence to the first amyloidogenic polypeptide binds to form a higher ordered aggregate are provided. In some embodiments the first and second amyloidogenic polypeptides are no more than 50%, 60%, 70%, 80%, 90%, or up to 95% identical. In some embodiments the first and second amyloidogenic polypeptides are no more than 50% identical, e.g., between 20% and 40% identical.

The term "CsgA polypeptide" as used herein encompasses any polypeptide whose sequence comprises or consists of the sequence of a naturally occurring bacterial CsgA polypeptide. In some embodiments, the CsgA polypeptide has the amino acid sequence:

```
                                                (SEQ ID NO: 1)
MKLLKVAAIAAIVFSGSALAGVVPQYGGGGNHGGGGNNSGPNSELNIYQY

GGGNSALALQTDARNSDLTITQHGGGNGADVGQGSDDSSIDLTQRGFGNS

ATLDQWNGKNSEMTVKQFGGGNGAAVDQTASNSSVNVTQVGFGNNATAHQ

Y
```

The term "CsgA polypeptide" also encompasses polypeptides that are variants of a polypeptide whose sequence comprises or consists of the sequence of a naturally occurring bacterial CsgA polypeptide, which are referred to as "CsgA polypeptide variants." In some embodiments a CsgA polypeptide variant is at least 20%, 30%, 40%, 50%, 60%, 70%, 80%, 90%, 95%, 96%, 97%, 98%, 99% or 100% identical to or similar to a naturally occurring CsgA polypeptide (SEQ ID NO: 1) across the length of the CsgA polypeptide variant. In some embodiments, a CsgA polypeptide variant is at least 20%, 30%, 40%, 50%, 60%, 70%, 80%, 90%, 95%, 96%, 97%, 98%, 99% or 100% identical to or similar to a half (or 50%) of the length of a naturally occurring CsgA polypeptide (SEQ ID NO: 1).

In some embodiments a "CsgA peptide" is also used interchangeably herein as a "CsgA polypeptide fragment" and is at least 5% or 10%, 20%, 30%, 40%, 50%, 60%, 70%, 80%, 90%, 95%, 96%, 97%, 98%, 99% or 100% as long as a naturally occurring CsgA polypeptide. In some embodiments a CsgA peptide is at least 8-10 amino acids long. In some embodiments, a CsgA peptide is at least 8-10 amino acids long of a variant of a CsgA polypeptide. In some embodiments, a CsgA peptide is at least 6, 7, 8, 9, 10, 11, 12, 13, 14, 15, 16, 17, 18, 19, 20 or more than 20 amino acids long of a naturally occurring CsgA polypeptide or a variant of a CsgA polypeptide. In some embodiments, a CsgA peptide is at least 6, 7, 8, 9, 10, 11, 12, 13, 14, 15, 16, 17, 18, 19, 20 or more than 20 amino acids long of a naturally occurring CsgA polypeptide where at least one amino acid has been modified (i.e. by substitution, deletion or addition of an amino acid or amino acid analogue). In some embodiments, a CsgA peptide is at least 6, 7, 8, 9, 10, 11, 12, 13, 14, 15, 16, 17, 18, 19, 20 or more than 20 amino acids long of a naturally occurring CsgA polypeptide where at least 1, 2, 3, 4, 5 or more than 5 amino acids has been modified (i.e. by substitution, deletion or addition of an amino acid or amino acid analogue). In some embodiments, a CsgA peptide is at least 6, 7, 8, 9, 10, 11, 12, 13, 14, 15, 16, 17, 18, 19, 20 or more than 20 amino acids long of a naturally occurring CsgA polypeptide where at least 1, 2, 3, 4, 5 or more than 5 amino acids has been added to the N-terminus or C-terminus or both of the CsgA peptide.

The term "CsgB polypeptide" as used herein encompasses any polypeptide whose sequence comprises or consists of the sequence of a naturally occurring bacterial CsgB polypeptide. In some embodiments, the CsgB polypeptide has the amino acid sequence:

```
                                                (SEQ ID NO: 2)
MKNKLLFMMLTILGAPGIAAAAGYDLANSEYNFAVNELSKSSFNQAAIIG

QAGTNNSAQLRQGGSKLLAVVAQEGSSNRAKIDQTGDYNLAYIDQAGSAN

DASISQGAYGNTAMIIQKGSGNKANITQYGTQKTAIVVQRQSQMAIRVTQ

R
```

The term "CsgB polypeptide" also encompasses polypeptides that are variants of a polypeptide whose sequence comprises or consists of the sequence of a naturally occurring bacterial CsgB polypeptide, which are referred to as "CsgB polypeptide variants." CsgB is a nucleator protein that facilitates the efficient assembly of CsgA. In some embodiments a CsgB polypeptide variant is at least 20%, 30%, 40%, 50%, 60%, 70%, 80%, 90%, 95%, 96%, 97%, 98%, 99% or 100% identical to or similar to a naturally occurring CsgB polypeptide (SEQ ID NO: 2) across the length of the CsgB polypeptide variant. In some embodiments, a CsgB polypeptide variant is at least 20%, 30%, 40%, 50%, 60%, 70%, 80%, 90%, 95%, 96%, 97%, 98%, 99% or 100% identical to or similar to a half (or 50%) of the length of a naturally occurring CsgB polypeptide (SEQ ID NO: 2).

In some embodiments a "CsgB peptide" is also used interchangeably herein as a "CsgB polypeptide fragment" and is at least 5% or 10%, 20%, 30%, 40%, 50%, 60%, 70%, 80%, 90%, 95%, 96%, 97%, 98%, 99% or 100% as long as a naturally occurring CsgB polypeptide. In some embodiments a CsgB peptide is at least 8-10 amino acids long. In some embodiments, a CsgB peptide is at least 8-10 amino acids long of a variant of a CsgB polypeptide. In some embodiments, a CsgB peptide is at least 6, 7, 8, 9, 10, 11, 12, 13, 14, 15, 16, 17, 18, 19, 20 or more than 20 amino acids long of a naturally occurring CsgB polypeptide or a variant of a CsgB polypeptide. In some embodiments, a CsgB peptide is at least 6, 7, 8, 9, 10, 11, 12, 13, 14, 15, 16, 17, 18, 19, 20 or more than 20 amino acids long of a naturally occurring CsgB polypeptide where at least one amino acid has been modified (i.e. by substitution, deletion or addition of an amino acid or amino acid analogue). In some embodiments, a CsgB peptide is at least 6, 7, 8, 9, 10, 11, 12, 13, 14, 15, 16, 17, 18, 19, 20 or more than 20 amino acids long of a naturally occurring CsgB polypeptide where at least 1, 2, 3, 4, 5 or more than 5 amino acids has been modified (i.e. by substitution, deletion or addition of an amino acid or amino acid analogue). In some embodiments, a CsgB peptide is at least 6, 7, 8, 9, 10, 11, 12, 13, 14, 15, 16, 17, 18, 19, 20 or more than 20 amino acids long of a naturally occurring CsgB polypeptide where at least 1, 2, 3, 4, 5 or more than 5 amino acids has been added to the N-terminus or C-terminus or both of the CsgB peptide.

The term "membrane-free," as used herein, refers to a composition that does not contain bacterial membranes.

"Peptides" are defined herein as organic compounds comprising a chain of two or more amino acids covalently joined by peptide bonds. Peptides may be referred to with respect to the number of constituent amino acids, i.e., a dipeptide contains two amino acid residues, a tripeptide contains three, etc. A "peptide" as used in the presently claimed invention is intended to refer to a moiety with a molecular weight of less than 20,000 Daltons, preferably less than 17,000 Daltons.

As used herein, "peptidomimetic" means a small protein-like chain designed to mimic a peptide. A peptidomimetic may be a backbone modified peptide, any polyamide or other polymeric structure resembling peptides, peptides containing non-natural amino acid residues or a peptide derivative.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, norvaline, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "hydrophobic residues" and grammatical equivalents means valine, isoleucine, leucine, methionine, phenylalanine, tyrosine, tryptophan, and functional equivalents thereof.

The term "polar residues" and grammatical equivalents means aspartic acid, asparagine, glutamic acid, glutamine, lysine, arginine, histidine, serine, and functional equivalents thereof.

The term "peptide bond" means a covalent amide linkage formed by loss of a molecule of water between the carboxyl group of one amino acid and the amino group of a second amino acid.

The term "peptide backbone" means the chain of atoms of a peptide comprising the carboxamide groups that are the peptide bonds together with the atoms of the amino acids that link the carboxyl and amino groups of the amino acid (usually the α-carbon of an α-aminoacid).

The term "side chain" means groups that are attached to the peptide backbone, and typically refers to the group attached to the α-carbon of an α-amino acid. For example, for the side chains of the proteinogenic amino acids include: methyl (alanine), hydroxymethyl (serine), benzyl (phenylalanine), mercaptomethyl (cysteine), and carboxymethyl (aspartic acid).

The term "derivative" as applied to compounds comprising a peptide chain means a compound wherein one or more of the amino, hydroxyl, or carboxyl groups in a side chain of the peptide, or the terminal amino or carboxyl groups, is modified to a derivative functional group. An amino group may be derivatized as an amide (such as an alkyl carboxamide, acetamide), a carbamate (such as an alkyl carbamate, e.g. methyl carbamate or t-butylcarbamate), or a urea. A hydroxyl group may be derivatized as an ester (such as an alkanoate, e.g. acetate, propionate, or an arenecarboxylate, e.g. benzoate), a carbamate (such as an alkyl carbamate, e.g. methyl carbamate), a carbonate (such as an alkyl carbonate, e.g. ethyl carbonate. A carboxyl group may be derivatized as an ester (such as an alkyl ester, e.g. ethyl ester) or an amide (e.g. primary carboxamide, an N-alkyl secondary carboxamide, or an N,N-dialkylcarboxamide). The person skilled in the art will appreciate that derivatives of the peptide will be expected to result in retention of the properties of the parent peptide, either because the incorporation of the derivative group does not change the properties of the peptide, or the derivatizing group is removed in vivo (e.g. via metabolism). Preferred embodiments of the invention are those wherein three or fewer of the amino, carboxyl, and hydroxyl groups, and preferably two or fewer, or one or none, are modified to a derivative functional group. The term "derivative" also includes salts, includes salts of derivatives.

"Natural amino acid" is used to refer to an amino acid which exists in nature. As used herein, amino acids are represented by the full name thereof, by the three-letter code, as well as the one-letter code corresponding thereto, as shown in the table below. The structure of amino acids and their abbreviations can be found in the chemical literature, such as in Stryer, 1988, "Biochemistry", $3^{rd}$ Ed., W.H. Freeman & Co., NY, NY.

| Full Name | Three-Letter Code | One-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Non-natural amino acid" is used to refer to an amino acid which does not exist on its own in nature, but rather, has been synthesized or created by man. Examples of non-natural amino acids include iodinated tyrosine, methylated tyrosine, glycosylated serine, glycosylated threonine, azetidine-2-carboxylic acid, 3,4-dehydroproline, perthiaproline, canavanine, ethionine, norleucine, selenomethionine, animohexanoic acid, telluromethionine, homoallylglycine, and homopropargylglycine. D-amino acids are also examples of non-natural amino acids.

As used herein, the term "hydroxylated acyclic amino acid" refers to an acyclic amino acid that contains at least one alcohol hydroxyl group in its structure. Preferred, but non-limiting, examples of hydroxylated acyclic amino acid are serine, (D)-serine, threonine, (D)-threonine, (L)-allo-threonine, (D)-allo-threonine, (L)-isoserine, (D)-isoserine, (L)-β-homoserine, (D)-β-homoserine, (L)-homoserine, and (D)-homoserine.

As used herein, the term "aliphatic amino acid" refers to an amino acid which carbon chain is aliphatic in nature. Non-limiting examples of aliphatic amino acids are alanine, arginine, asparagine, aspartic acid, cysteine, glutamic acid, glutamine, glycine, isoleucine, leucine, lysine, methionine, proline, serine, threonine, valine, Nva, NvaNH$_2$, Acp, AcpNH$_2$, Dpr(Ac), Dbu, N-MeArg, βAla, βAlaNH$_2$, Apa, and AlloThr. Preferred aliphatic amino acids within the present application are βAla, βAlaNH$_2$, Acp and AcpNH$_2$.

The term "peptide transduction domain" is used to indicate a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be a peptide chain, an amino acid, or any group having at least two functional groups and capable of forming covalent bond to each of the two peptide chains.

An "acetylated amino acid" as used herein refers to an amino acid having an acetyl moiety in its side chain.

As used herein, "isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as a host cell for example. By "isolated amyloid peptide" is not only meant an amyloid peptide of bacterial origin that forms aggregates, but "isolated amyloid peptide" is also meant to include aggregates of such peptides/proteins also known as "amyloids."

As used herein, "naturally occurring" or "wild type" or "wt" or "native" and grammatical equivalents thereof mean an amino acid sequence or a nucleotide sequence that is found in nature, including allelic variations.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies that may be used in the practice of the present invention may exist in a variety of forms including, for example, polyclonal antibodies, monoclonal, Fv, Fab and F(ab)$_2$, as well as single chain antibodies and humanized antibodies (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.; Houston et al., 1988, *Proc. Natl. Acad. Sci. USA* 85:5879-5883; Bird et al., 1988, *Science* 242:423-426).

The term "control" or "reference standard" describes a material comprising a level of a bacterial amyloid, such that the control or reference standard may serve as a comparator against which a sample can be compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence which is identical to the mRNA sequence and is usually provided in sequence listings, and the non-coding strand, used as the template for transcription of a gene or cDNA, can be referred to as encoding the protein or other product of that gene or cDNA.

"Gene expression" or "expression" as used herein refers to the process by which information from a gene is made into a functional gene product, such as RNA or protein. Thus, the "level of expression" of a gene product of a marker gene, in a sample of interest, refers to the level of RNA, particularly the level of mRNA, or the level of the encoded protein, and is not intended to be limited to either, unless so specified. "Protein expression," as used herein refers to the level of protein.

The term "gene" refers to a nucleic acid (e.g., DNA) sequence that comprises coding sequences necessary for the production of a polypeptide, precursor, or RNA (e.g., mRNA, rRNA, tRNA). The term "gene" encompasses both cDNA and genomic forms of a gene.

The term "treatment" as used herein refers to the management or combating of a disease or disorder. The treatment may be prophylactic, or may take place after the subject has acquired the disease or disorder. The expressions "treat" and "treatment" and grammatical equivalents thereof mean administration of a substance to a subject with the purpose to cure, alleviate, relieve, remedy, prevent or ameliorate a disorder, or a disease state secondary to the disorder.

As used herein, an "instructional material" includes a publication, a recording, a diagram, or any other medium of expression, which can be used to communicate the usefulness of the invention in the kit for determining the progression of a disease. The instructional material of the kit of the invention may, for example, be affixed to a container, which contains a reagent of the invention or be shipped together with a container, which contains a reagent. Alternatively, the instructional material may be shipped separately from the container with the intention that the instructional material and the reagent be used cooperatively by the recipient.

"Measuring" or "measurement," or alternatively "detecting" or "detection," or alternatively "determining" or "determine" means assessing the presence, absence, quantity or amount of either a given substance within a sample, including the derivation of qualitative or quantitative concentration levels of such substances.

"Sample" or "biological sample" as used herein means a biological material that contains a substance under assay for determination of gene product expression level. The sample may contain any biological material suitable for detecting a bacterial amyloid protein, and may comprise cellular and/or non-cellular material.

DETAILED DESCRIPTION OF THE INVENTION

Provided is a method for the treatment of a subject having an inflammatory disease of the epithelium comprising the step of administering an effective amount of a composition comprising an isolated bacterial amyloid peptide to the subject.

Provided is a method for decreasing epithelium permeability in a tissue of a subject comprising epithelium comprising the step of administering an effective amount of a composition comprising an isolated bacterial amyloid peptide to the epithelium of the subject.

The modulation of intestinal epithelial barrier integrity is crucial for the maintenance of intestinal immune homeostasis. It has been unexpectedly found that epithelial permeability is decreased upon activation of the TLR2/PI3K pathway by curli amyloid fibrils. This is demonstrated in Example 3. The activation of TLR2 by curli fibrils in vivo was shown to decrease epithelium permeability and to reduce bacterial translocation in Example 4. Therefore, curli amyloid fibers may be administered to treat a subject having an inflammatory disease of the epithelium because by decreasing intestinal permeability, curli amyloid fibers help to maintain intestinal immune homeostasis and to protect the host from hyper-responsive inflammatory processes.

It was also unexpectedly found that curli fibers induce IL-10 production in the intestine after administration, as demonstrated in Example 5. This indicates that the administration of curli fibers leads to a stronger immune response.

DNA was found to be tightly associated with curli fibers in some bacterial biofilms, as demonstrated in Example 6. It was also unexpectedly found that DNA accelerates curli fiber polymerization, as demonstrated in Example 7. Thus, in some embodiments the composition comprising an isolated bacterial amyloid peptide comprises DNA.

Preparation of Isolated Bacterial Amyloid Peptides of the Invention

The peptides utilized in the methods of the invention may be prepared by methods known to the person skilled in the art of peptide synthesis and biotechnology.

Peptides utilized in the practice of the present invention may be natural peptides, recombinant peptides or synthetic peptides. They may also be chemically synthesized, using, for example, solid phase synthesis methods. Additionally, peptide transduction domains appended to peptides of the invention may be natural or synthetic peptides, and may be either prepared by isolation from natural sources or may be synthesized.

Peptides utilized in the methods of the present invention may be isolated from the bacteria in which they are synthesized. In some embodiments, the peptides utilized in the methods of the present invention are isolated from the bacteria in which they are synthesized as follows. Bacterial cells are removed from T-medium plates and lysed by sonication. This is followed by enzymatic digestion and preparative sodium dodecyl sulphate-gel electrophoresis (SDS-PAGE). Insoluble material (curli fibrils) retained in the well of the SDS-PAGE gel are collected after the electrophoresis is complete. (Collinson, S. K., L. Emody, K. H. Muller, T. J. Trust, and W. W. Kay. 1991. Purification and characterization of thin, aggregative fimbriae from *Salmonella enteritidis*. *Journal of Bacteriology* 173:4773-4781).

The peptides may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage reagents, e.g., trifluoroacetic acid (TFA), HCl in dioxane, boron tris-(trifluoroacetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

In an embodiment, the peptide synthesis method may follow Merrifield solid-phase procedures. See Merrifield, *J. Am. Chem. Soc.,* 1963, 85, 2149-54 and *Science,* 1965, 50, 178-85. Additional information about the-solid phase synthetic procedure can be obtained from the treatises *Solid Phase Peptide Synthesis: A Practical Approach* by E. Atherton and R. C. Sheppard (Oxford University Press, 1989, *Solid phase peptide synthesis*, by J. M. Stewart and J. D. Young, (2nd edition, Pierce Chemical Company, Rockford, 1984), and the review chapters by R. Merrifield in *Advances in Enzymology* 32:221-296, edited by F. F. Nold (Interscience Publishers, New York, 1969) and by B. W. Erickson and R. Merrifield in *The Proteins* Vol. 2, pp. 255 et seq., edited by Neurath and Hill, (Academic Press, New York, 1976). Peptide synthesis may follow synthetic techniques such as those set forth in Fields et al., *Introduction to Peptide Synthesis, in Current Protocols in Molecular Biology* (Chapter 11, Unit 11.15; John Wiley and Sons, 2008) and Amblard et al. (2006, Molecular Biotechnology, 33:239-254).

The synthesis of peptides by solution methods is described in The Proteins, Vol. 11, edited by Neurath et al. ($3^{rd}$ Edition, Academic Press 1976). Other general references to the synthesis of peptides include: *Peptide Synthesis Protocols*, edited by M. W. Pennington and Ben M. Dunn (Humana Press 1994), *Principles of Peptide Synthesis*, by Miklos Bodanszky ($2^{nd}$ edition, Springer-Verlag, 1993), and *Chemical Approaches to the Synthesis of Peptides and Proteins* by Paul Lloyd-Williams, F. Albericio, E. Giralt (CRC Press 1997), and *Synthetic Peptides: A User's Guide*, edited by G. Grant (Oxford University Press, 2002).

Alternatively, peptides may be prepared utilizing recombinant DNA technology, which comprises combining a nucleic acid encoding peptides of formula I in a suitable vector, inserting the resulting vector into a suitable host cell, recovering the peptide subsequently produced by the host cell, and purifying the polypeptide recovered. The required techniques of recombinant DNA and protein technology are known to the ordinary skilled artisan. General methods for the cloning and expression of recombinant molecules are described in *Molecular Cloning* by Sambrook et al. (Cold Spring Harbor Laboratories, Second Ed., 1989) and in *Current Protocols in Molecular Biology* by Ausubel (Wiley and Sons, 1987).

The nucleic acid encoding a desired peptide may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

Promoters that may be used in the synthesis of peptides of the present invention include both constitutive promoters and inducible promoters. The promoters may be prokaryotic or eukaryotic, depending on the host. Non-limiting examples of promoters that may be used are: the T7 lac promoter, the T7 promoter, pBAD, the tet promoter, the Lac promoter, the Trc promoter, the Trc promoter and the PL promoter, all of which can be utilized when trying to express the protein in a bacterial cell such as *E. coli*, for example. If one is utilizing an insect as the host cell, promoters such as polyhydrin, P10, MT, Ac5 and Op1E2 may be utilized. If one prefers to express the protein in a virus, pCMV, pUbC and pU6 may be used as promoters. Promoters which may be utilized in mammalian cells include, for example, CMV, U6, EF-1, pCMV-2xTetO2, pUbC, SV40, b-casein and RSV. Suitable yeast promoters include AOX1, GAP, AUG1, GAL1, nmt1, nmt41, nmt81 and TEF1. The choice of sequences present in the construct is dependent upon the desired expression products as well as the nature of the host cell.

Once a vector has been constructed comprising the nucleic acid encoding a desired peptide may be operatively linked to one or more regulatory regions, it may then be introduced into the host cell of choice by methods known to those of ordinary skill in the art, including, for example, transfection, transformation and electroporation (see Molecular Cloning: A Laboratory Manual, 2nd ed., Vol. 1-3, ed. Sambrook et al., Cold Spring Harbor Laboratory Press (1989)). The host cell is then cultured under suitable conditions permitting the expression of the nucleotide sequences leading to the production of the desired, encoded curli fibril protein which is then recovered and purified.

Examples of suitable prokaryotic host cells include, for example, bacteria such as *Escherichia coli, Bacillus* sp., *Streptococcus* sp., *Lactococcus* sp. and *Lactobacillus* sp. Examples of suitable eukaryotic host cells include, for example, insect cells (e.g., SF9, SF21 and Hi5), yeast cells, *S. pombe*, mammalian cells and *Drosophila* cells.

Expression in a host cell can be accomplished in a transient or stable fashion. Transient expression can occur from introduced constructs which contain expression signals functional in the host cell, but which constructs do not replicate and rarely integrate in the host cell, or when the host cell is not proliferating. Transient expression also can be accomplished by introducing the activity of a regulatable promoter operably linked to the gene of interest. Stable expression can be achieved by introduction of a construct that can integrate into the host genome or that autonomously replicates in the host cell. Stable expression of the gene of interest can be selected through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the protein of interest. More specifically, once the above-described vector is created, it may be inserted into the pronucleus of an embryo. The embryo may then be implanted into a recipient female. Alternatively, a nuclear transfer method could also be utilized (Schnieke et al., Science 278:2130-2133 (1997)). Gestation and birth are then permitted (see, e.g., U.S. Pat. Nos. 5,750,176 and 5,700, 671). The mammal utilized as host may a mouse, a rat, a rabbit, a pig, a goat, a sheep, a horse or a cow, for example. However, any mammal may be used provided it has the ability to incorporate DNA encoding the protein of interest into its genome.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolation of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, New York (1997)).

The peptides of the invention, whether prepared by chemical synthesis or recombinant DNA technology, may be purified using known techniques, for example preparative HPLC, FPLC, affinity chromatography, as well as other chromatographic methods. Isolated peptides may then be assessed for biological activity according to the methods described herein, as well as by any methods known to the skilled artisan.

For synthetic techniques, peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent.

Curli Fibers Complexed with DNA

In some embodiments the isolated bacterial amyloid proteins, synthetic curli peptides or fragments of synthetic curli peptides, are complexed with DNA. The DNA may be of synthetic origin or non-synthetic orgin. In some embodiments the DNA is high in CpG content. In further embodiments the DNA that is high in CpG content has the following sequence:

(SEQ ID NO: 3)
5'-tccatgacgttcctgacgtt-3'

In further embodiments, the DNA is genomic DNA of heterologous or homologous origin. In yet further embodiments the DNA is a synthetic DNA sequence used as a TLR9 agonist:

(SEQ ID NO: 4)
5'-tccatgacgttcctgacgtt-3'

In some embodiments the DNA accelerates the polymerization of the isolated bacterial amyloid proteins, synthetic curli peptides or fragments of synthetic curli peptides.

In some embodiments the curli peptide fragment comprises the fourth and fifth repeats of CsgA.

Pharmaceutical Compositions

The methods of the present invention may comprise administering the isolated bacterial amyloid proteins in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The active ingredient is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18$^{th}$ Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 1 to about 1000 mg, preferably from about 7.5 to about 500 mg. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled release of the active ingredient may be stimulated by various inducers, for example pH, temperature, enzymes, water, or other physiological conditions or peptides. Various mechanisms of drug release exist. For example, in one embodiment, the controlled-release component may swell and form porous openings large enough to release the active ingredient after administration to a patient. The term "controlled-release component" in the context of the present invention is defined herein as a peptide or peptides, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the bacterial amyloid peptides that are suitable for administration intranasally or by inhalation are of particular interest.

The peptides of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 μg to 20 mg of the compound of the invention per actuation and the actuation volume may vary from 1 μL, to 100 μL. A typical formulation may comprise the compound of the invention, propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

Methods of Treatment using Isolated Bacterial Amyloid

Compositions comprising an isolated bacterial amyloid peptide are useful for treating inflammatory disorders or diseases of the epithelium. The peptides activate TLR2 and decrease epithelial permeability. Accordingly, the peptides may be used to treat conditions including, but not limited to, epithelial inflammatory disorders or diseases.

Therefore, an individual who is in need of treatment with a compound according to the invention can be an individual who is suffering from one or more inflammatory disorders or diseases, among other disorders or diseases.

Provided is a method of treating an individual suffering from an inflammatory disease of the epithelium comprising the step of administering an effective amount of a composition comprising an isolated bacterial amyloid peptide to the subject.

The invention is also directed to the use in medicine of a composition comprising an isolated bacterial amyloid peptide, or a pharmaceutically acceptable salt thereof.

The invention is also directed to the use of a composition comprising an isolated bacterial amyloid peptide, or a pharmaceutically acceptable salt thereof, in the preparation of a medicament for treatment of an inflammatory disease of the epithelium.

The invention is also directed to a composition comprising an isolated bacterial amyloid peptide, or a pharmaceutically acceptable salt thereof, for use in the preparation of a medicament for treatment of an inflammatory disease of the epithelium.

Particular and preferred embodiments of this aspect of the invention are those wherein the composition comprising an isolated bacterial amyloid peptide used in the method of treatment, either alone or as part of a composition, or as a component of the antibody conjugate, is a particular or preferred embodiment of the composition comprising an isolated bacterial amyloid peptide in the description of the compositions of the invention as provided herein.

The amyloid peptides may be administered to individuals (mammals, including animals and humans) afflicted with an inflammatory disease of the epithelium such as an inflammatory disease of the bowel or an inflammatory disease of the skin. In a particular embodiment of the invention, the individual treated is a human.

The amyloid peptides are believed effective against a broad range of inflammatory diseases, including but not limited to the following: IBD, including Crohn's disease and ulcerative colitis, inflammatory skin disorders or diseases, including psoriasis, atopic dermatitis/eczema, contact dermatitis, aphthous ulcers and peptic ulcer disease.

Administration of Isolated Bacterial Amyloid

In an embodiment of the invention, the compositions comprising an isolated bacterial amyloid peptide are administered by way of a continuous-release transdermal patch. However, the compositions may be administered by any route, including local, oral, rectal, pulmonary, sublingual, and parenteral administration. Parenteral administration includes, for example, intravenous, intramuscular, intraarterial, intravesical (e.g., to the bladder), intradermal, transdermal, topical or subcutaneous administration.

The administration can comprise systemic administration or local administration. In one embodiment, an epithelium is treated, wherein the epithelium arises in one or more of the following tissues: blood vessels, ducts of submandibular glands, attached gingival, dorsum of tongue, hard palate, oesophagus, stomach, small intestine, large intestine, rectum, anus, gallbladder, thyroid follicles, ependyma, lymph vessel, skin, sweat gland ducts, mesothelium of body cavities, ovaries, fallopian tubes, endometrium, cervix, vagina, labia majora, tubuli recti, rete testis, ductuli efferentes, epididymis, vas deferens, ejaculatory duct, bulbourethral glands, seminal vesicle, oropharynx, larynx, trachea, respiratory bronchioles, cornea, nose, proximal convoluted tubule of the kidney, ascending thin limb of the kidney, distal convoluted tubule of the kidney, collecting duct of the kidney, renal pelvis, ureter, urinary bladder, prostatic urethra, penile urethra or external urethral orifice. Treatment of such tissues may be by administration of systemic or local bacterial amyloid protein.

Typically it is contemplated that treatment would be given at least once per day, typically once, twice, three times or four times per day with the doses given at equal intervals throughout the day and night in order to maintain a constant presence of the composition comprising an isolated bacterial amyloid peptide in order to induce sufficient decrease in epithelial permeability, or to sufficiently treat the inflammation. However, the skilled artisan will be aware that a treatment schedule can be optimized for any given patient, and that administration of compound may occur less frequently than once per day.

One or more amyloid peptides may be administered simultaneously, by the same or different routes, or at different times during treatment. The peptides of the invention may also be prescribed to be taken in combination with other drugs used to treat inflammatory disorders or diseases. When used in such combinations, amyloid peptides and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the peptides no longer produce a beneficial effect. The treating physician will know how to increase, decrease, or interrupt treatment based on patient response.

The specific dose of an amyloid peptide according to the invention to obtain therapeutic benefit for treatment of a cellular inflammatory disorder or disease will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 5 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Recombinant Bacterium Comprising a Heterologous Polynucleotide that Encodes a Heterologous Bacterial Amyloid Peptide Recombinant bacterial cells may be genetically modified to express a heterologous bacterial amyloid peptide. In some embodiments, the recombinant bacterial cells may be genetically modified by the introduction of a heterologous polynucleotide that encodes a heterologous bacterial amyloid peptide. In some embodiments, an expression plasmid comprising a heterologous polynucleotide that encodes a heterologous bacterial amyloid peptide may be used. In further embodiments, the heterologous polynucleotide that encodes a heterologous bacterial amyloid peptide may be integrated into the bacteria's chromosome.

Any bacteria of interest can be used in the methods and compositions described herein. In some embodiments, the bacterium comprises a probiotic bacterium. The term "probiotic" as used herein refers to live microorganisms, which when administered in adequate amounts confer a health benefit on a host or at least one organism that contributes to the health and balance of the intestinal tract of a subject. Such organisms are also referred to as "friendly," "beneficial" or "good" bacteria, which when ingested by a subject assists in the maintenance of a healthy intestinal tract and assists in partially or completely alleviating one or more symptoms of an illness and/or disease. As used herein, "probiotic properties" comprises enhanced gut function and stability; improved protection against infectious and non-infectious diseases; immune system modulation; alleviated lactose intolerance; improved digestion and nutrient absorption; reduced blood cholesterol; reduced allergy risk; and reduced risk of urinary tract infection. In some embodiments, probiotic properties comprise an increase in anti-inflammatory cytokine production in the subject receiving the probiotic bacterium, a decrease in pro-inflammatory cytokine production in the subject receiving the probiotic bacterium, or an increase in the ratio of anti-inflammatory to pro-inflammatory cytokine production in the subject receiving the probiotic bacterium.

In some embodiments, the recombinant bacterium is *E. coli* or another member of the Enterobacteriaceae family. In further embodiments, the recombinant bacterium is a lactic acid bacterium. In further embodiments, the recombinant bacterium is *Aerococcus, Bifidobacterium, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus*, and *Weissella*.

In some embodiments, *Lactobacillus* is used. By "*Lactobacillus*" is meant any bacteria from the genus *Lactobacillus*, including but not limited to *L. casei, L. parcasei, L. reuteri, L. rhamnosus, L. johnsonni, L. gasseri, L. acidophilus, L. plantarum, L. fermentum, L. salivarius, L. bulgaricus* and *L. acidophilus* NCFM.

In preferred embodiments, *Lactobacillus, Bifidobacterium* or *Lactococcus* is used. The advantages of using these strains include: (1) these strains are generally recognized as safe (GRAS), (2) curli help bacteria to colonize the gut better so these safe organisms would colonize the gut better and (3) curli fibers produced by these organisms would provide beneficial effects in patients/people suffering from gastrointestinal inflammation or intestinal epithelial barrier defects.

Bacterial cells described herein can be cultured in suitable media, and transformed as described generally in Sambrook et al. (1989) *Molecular Cloning, A Laboratory Manual* (2d ed., Cold Spring Harbor Laboratory Press, Cold Spring Harbor, N.Y.).

Pharmaceutical Compositions Comprising the Recombinant Bacterium

In some embodiments, the recombinant bacterium of the invention is administered to a subject in the form of a nutraceutical composition such as a nutritional supplement and/or food additive. In some embodiments, the recombinant bacterium of the invention is administered to a subject in the form of a pharmaceutical composition. The administration may comprise a single dose or multiple dose administration, as described elsewhere herein.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or a syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

As used herein, the term "pharmaceutical composition" could be formulated as a food composition, a dietary supplement, a functional food, a medical food or a nutritional product as long as the required effect is achieved, i.e. treatment or prevention of an inflammatory disease of the epithelium. Said food composition may be chosen from the group consisting of beverages, yogurts, juices, ice creams, breads, biscuits, crackers, cereals, health bars, spreads and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins.

The pharmaceutical composition according to the invention, used according to the invention or produced according to the invention may also comprise other substances, such as an inert vehicle, or pharmaceutically acceptable adjuvants, carriers, preservatives etc., which are well known in the art.

Administration of Recombinant Bacterium

The quantity to be administered, both according to number of treatments and unit dose, depends on the subject to be treated, the state of the subject and the effect desired. Precise amounts of the therapeutic composition also depend on the judgment of the practitioner and are peculiar to each individual. Generally, the dosage of recombinant bacteria will vary depending upon such factors as the patient's age, weight, height, sex, general medical condition and previous medical history. In specific embodiments, it may be desirable to administer the bacterium in the range of about $10^4$ to about $10^{12}$ CFU (colony forming units), $10^5$ to $10^{11}$ CFU, $10^6$ to $10^{10}$ CFU, $10^8$ to $10^{10}$ CFU or $10^8$ to $10^{12}$ CFU.

In some embodiments, the method comprises administration of multiple doses of the bacterium. The method may comprise administration of 1, 2, 3, 4, 5, 6, 7, 8, 9, 10, 15, 20, 25, 30, 35, 40 or more therapeutically effective doses of a composition comprising the bacterium as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to reduce or prevent an inflammatory response and thereby treat or prevent a gastrointestinal disorder or disease. Moreover, treatment of a subject with a therapeutically effective amount of the recombinant bacterium of the invention can include a single treatment or can include a series of treatments. It will also be appreciated that the effective dosage of a bacterium used for treatment may increase or decrease over the course of a particular treatment. Changes in dosage may result and become apparent from the results of diagnostic assays for detecting inflammation known in the art and described therein.

In an embodiment of the invention, the compositions comprising a recombinant bacterium of the invention are administered by way of a continuous-release transdermal patch. However, the compositions may be administered by any route, including local, oral, rectal, pulmonary, sublingual, and parenteral administration. Parenteral administration includes, for example, intravenous, intramuscular, intraarterial, intravesical (e.g., to the bladder), intradermal, transdermal, topical or subcutaneous administration.

The administration can comprise systemic administration or local administration. In one embodiment, an epithelium is treated, wherein the epithelium arises in one or more of the following tissues: blood vessels, ducts of submandibular glands, attached gingival, dorsum of tongue, hard palate, oesophagus, stomach, small intestine, large intestine, rectum, anus, gallbladder, thyroid follicles, ependyma, lymph vessel, skin, sweat gland ducts, mesothelium of body cavities, ovaries, fallopian tubes, endometrium, cervix, vagina, labia majora, tubuli recti, rete testis, ductuli efferentes, epididymis, vas deferens, ejaculatory duct, bulbourethral glands, seminal vesicle, oropharynx, larynx, trachea, respiratory bronchioles, cornea, nose, proximal convoluted tubule of the kidney, ascending thin limb of the kidney, distal convoluted tubule of the kidney, collecting duct of the kidney, renal pelvis, ureter, urinary bladder, prostatic urethra, penile urethra or external urethral orifice. Treatment of such tissues may be by administration of systemic or local recombinant bacterium.

Typically it is contemplated that treatment would be given at least once per day, typically once, twice, three times or four times per day with the doses given at equal intervals throughout the day and night in order to maintain a constant presence of the composition comprising recombinant bacterium in order to induce sufficient decrease in epithelial permeability, or to sufficiently treat the inflammation. However, the skilled artisan will be aware that a treatment schedule can be optimized for any given patient, and that administration of compound may occur less frequently than once per day.

One or more recombinant bacteria of the invention may be administered simultaneously, by the same or different routes, or at different times during treatment. The recombinant bacteria of the invention may also be prescribed to be taken in combination with other drugs used to treat inflammatory disorders or diseases. When used in such combinations, recombinant bacteria and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the recombinant bacteria no longer produce a beneficial effect. The treating physician will know how to increase, decrease, or interrupt treatment based on patient response.

The specific dose of a recombinant bacterium according to the invention to obtain therapeutic benefit for treatment of a cellular inflammatory disorder or disease will, of course, be determined by the particular circumstances of the individual patient including the size, weight, age and sex of the patient, the nature and stage of the disease, the aggressiveness of the disease, and the route of administration of the compound.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the peptides of the present invention and practice the claimed methods. The following working examples therefore, specifically point out the preferred embodiments of the present invention, and are not to be construed as limiting in any way the remainder of the disclosure.

EXAMPLES

Example 1

TLR2 and TLR1 are Expressed by Polarized T-84 Epithelial Cells

To explore the immune responses generated against amyloid fibrils, a human colon carcinoma line, T-84, was used to determine if it expressed TLR2 and TLR1. When grown on permeable tissue culture inserts T-84 epithelial cells are able to differentiate and polarize to take on functional and morphological characteristics that are specific to the intestinal epithelium with apical microvilli and a basolateral surface that can be likened to the cellular surface in contact with the subepithelial lamina propria.

Materials and Methods

Cell Culture

The T-84 cells were obtained from American Type Culture Collection. T-84 cells were grown in DMEM/F12 (GIBCO) supplemented with 10% heat-inactivated fetal bovine serum (FBS; GIBCO). T-84 cells were grown to confluence on 0.4 µm permeable tissue culture inserts (Transwell; Corning) in a humidified incubator at 37° C. and 5% $CO_2$. T-84 cells achieved a polarized and differentiated state within 5-10 days and were used when Transepithelial resistance (TER) had reached >1500 $\Omega cm^2$.

PCR

To examine the expression of TLR1 and TLR2 by epithelial cells, T-84 cells were grown to confluence on permeable tissue culture inserts as described above. RNA was extracted in 0.5 ml of TriReagent. Following RNA isolation, 2 µg of total RNA was reverse-transcribed using MuLV Reverse Transcriptase, and 2 µl of cDNA was subjected to PCR amplification using a High Fidelity PCR supermix (Invitrogen) and the primers listed in Table 1. The following program was used for PCR amplification: 95° C. for 120 s, followed by 35 cycles of 95° C. for 60 s, 55-58° C. for 45 s (annealing temperatures were optimized for each TLR primer pair used) and 72° C. for 60 s. As a positive control, HeLa cells were stably transfected with a plasmid expressing either TLR1 or TLR2 as described previously (Tukel C et al., 2010. Toll-like receptors 1 and 2 cooperatively mediate immune responses to curli, a common amyloid from enterobacterial biofilms. *Cell Microbiol* 12:1495-1505). HeLa cells transfected with an empty vector were employed as a negative control. The resultant PCR products were then analysed on a 1.5% agarose gel.

TABLE 1

| Gene | Primer Sequence |
|---|---|
| hTLR1 | Forward: 5'-CTATACACCAAGTTGTCAGC-3' (SEQ ID NO: 5)<br>Reverse: 5'-GTCTCCAACTCAGTAACCTG-3' (SEQ ID NO: 6) |
| hTLR2 | Forward: 5'-GCCAAAGTCTTGATTGATTGG-3' (SEQ ID NO: 7)<br>Reverse: 5'-TTGAAGTTCTCCAGCTCCTG-3' (SEQ ID NO: 8) |

Statistical Analysis

Student's t test was used to calculate statistically significant differences (p<0.05). For analysis of bacterial numbers, values were logarithmically converted prior to statistical analysis.

Results:

RNA from T-84 cells was extracted and subjected to Reverse Transcription and PCR amplification. As controls, HeLa cells were transfected with an empty human expression vector (negative control) and a vector containing human TLR2 gene respectively. T-84 cells were found to express TLR2. Since curli amyloid fibrils have been reported to signal through TLR2 complexed with TLR1, TLR1 expression was also confirmed via PCR (FIG. 1A). Therefore, these experiments demonstrated that both TLR1 and TLR2 are expressed by T-84 cells, and these cells were thus selected for further study.

Example 2

Deletion of csgBA Decreases IL-8 Secretion by *S. Typhimurium* Infected Epithelial Cells In the following experiment, polarized T-84 epithelial cells were infected with wild type *S. Typhimurium* or its isogenic csgBA mutant and a gentamicin protection assay was performed to determine whether differences in host responses were due to differences in invasiveness between different bacterial strains.

Bacterial Strains

*S. Typhimurium* strain IR715 (wt) is a fully virulent, nalidixic acid-resistant strain derived from the ATCC strain 14028 (Stokiljkovic I et al., 1995. Ethanolamine utilization in *Salmonella typhimurium*: nucleotide sequence, protein expression, and mutational analysis of the cchA cchB eutE eutG eutH gene cluster. *J. Bacteriol* 177:1357-1366). CT16 is a mutant strain derived from IR715 and contains an unmarked csgBA deletion (i.e. a deletion of both CsgA and CsgB). To induce the expression of curli fibrils, the bacterial strains were grown on tryptone agar (T-medium) plates at 28° C. for 48 hours. For in vivo experiments, bacterial strains were grown overnight with shaking at 37° C. in Luria-Bertani (LB; Fisher Bioreagents) broth supplemented with Nalidixic acid (Fisher Bioreagents) at a final concentration of 0.05 mg/ml.

Invasion Assay

The invasion assay was carried out as described previously (Tukel C et al., 2005. CsgA is a pathogen-associated molecular pattern of *Salmonella enterica* serotype *Typhimurium* that is recognized by Toll-like receptor 2. *Mol Microbiol* 58:289-304). Briefly, polarized wells were infected with $3.5 \times 10^5$ (MOI of 7) of wild-type IR715 and the csgBA mutant CT16 bacterial strains. Bacteria were allowed to invade cells for an hour. This was then followed by replacement of the medium on both sides of the Transwell with medium containing 1 mg/ml gentamicin (Invitrogen) to eliminate extracellular bacteria and incubated for 1.5 hour. Epithelial cells were then lysed with 1% Triton-X (SIGMA). Cell lysates were then plated on LB agar plates supplemented with Nalidixic acid at a final concentration of 0.05 mg/ml. Invasion assays were repeated three times.

Figure 1B:
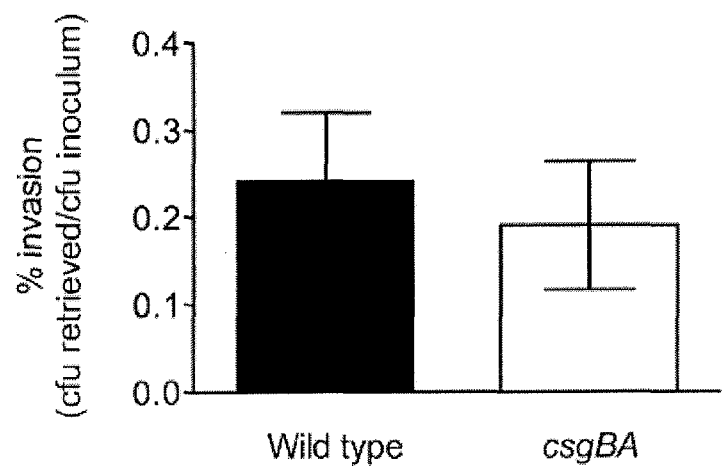
FIG. 1B illustrates the invasion of polarized T-84 epithelial cells by wild type *S. Typhimurium* and its isogenic csgBA mutant. Bacteria were grown under conditions optimal for expression of the curli fibrils prior to inoculating cells. The number of bacteria recovered from the gentamicin protection assay is expressed as the percentage of the number present in the inoculum. Data are shown as geometric means (bars) from three independent experiments±standard deviation.
Figure 1C:
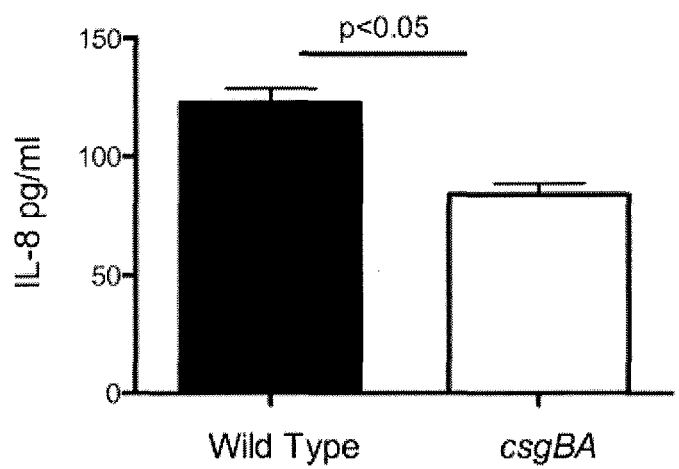
FIG. 1C illustrates the determination of IL-8 secretion in the supernatants of polarized T-84 cells infected with wild type *S. Typhimurium* and its isogenic csgBA mutant after 24 hours by ELISA.

Results:

We did not determine any difference in the invasiveness between the wild type *S. Typhimurium* and the csgBA mutant (FIG. 1B). However, increased levels of IL-8 were detected in the basolateral compartment of cells which were infected with the wild type *S. Typhimurium*, compared to cells infected with the csgBA mutant (FIG. 1C).

Example 3

Epithelial Integrity is Restored Through the Activation of TLR2/PI3K Pathway by Recognizing Curli Amyloid Fibrils on Bacteria The following experiments demonstrate the effect on epithelial integrity of the activation of the TLR2/PI3K pathway by curli amyloid fibrils.

Epithelial Integrity Assay

Polarized T-84 cells were infected with wild-type IR715 and the csgBA mutant CT16 as described above. 5 hours or 24 hours post-infection, 5 µl of 10 mg/ml Fluorescein isothiocyanate-labeled dextran (FITC-dextran; Average MW 3000-5000, SIGMA) was added to the apical side of the Transwell chamber. Two hours after the addition of FITC- Dextran, medium from the basolateral side of the Transwell chamber was collected and fluorescence intensity was measured using an Omega Plate Reader (BMG Labtech) at 485 nm excitation and 520 nm emission (Lambert C et al., 2005. Depletion of Caco-2 cell cholesterol disrupts barrier function by altering the detergent solubility and distribution of specific tight-junction proteins. *Biochem J* 387:553-560).

Figure 2A:
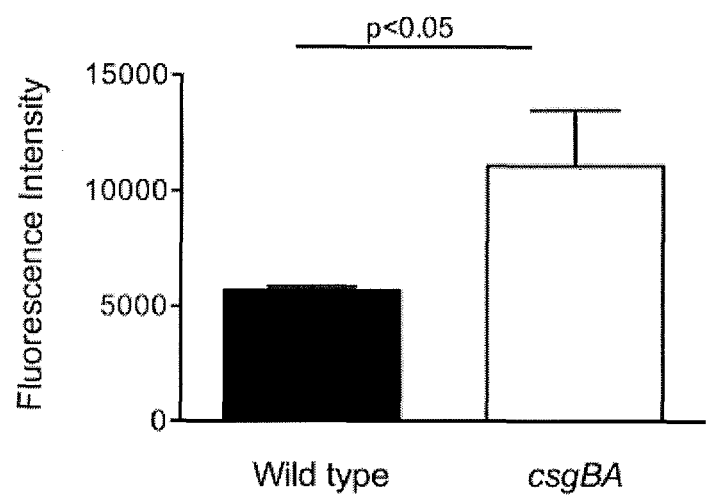
FIG. 2A illustrates the determination of epithelial permeability in polarized T-84 cells after infection with wild type *S. Typhimurium* and its isogenic csgBA mutant after 24 hours. FITC-dextran was added to the apical chamber for 2 hours. Fluorescence was then determined in the basolateral supernatants using a BMG Omega plate reader.
Figure 2B:
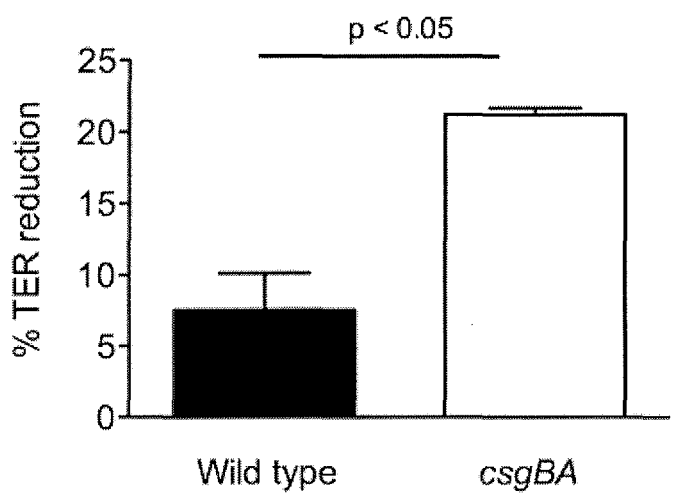
FIG. 2B illustrates the measure of changes in the transepithelial resistance (TER) 5 hours and 24 hours post infection and the calculation of percent TER.

To study the role played by flagellin and curli fibrils on intestinal epithelial integrity, flagellin (FLA-ST; Invivogen) was added to the Transwells basolaterally at a final concentration of 0.01 µg/ml. Purified curli fibrils from the *S. Typhimurium* msbB mutant (RPW3) were prepared according to an established protocol (Collinson S K et al, 1991. Purification and characterization of thin, aggregative fimbriae from *Salmonella enteridis*. *Journal of bacteriology* 173:4773-4781). Briefly, bacterial cells were removed from T-medium plates and lysed by sonication. This was followed by enzymatic digestion and preparative sodium dodecyl sulphate-polyacrylamide gel electrophoresis (SDS-PAGE). Insoluble material (curli fibrils) retained in the well of the SDS-PAGE gel was collected after the electrophoresis was complete. Curli fibrils (10 µg/ml) or the triacylated synthetic TLR2/TLR1 ligand $Pam_3CSK_4$ (0.1 µg/ml, Invivogen) were either added alone or simultaneously with basolateral flagellin treatment, to the apical chamber of the Transwell. To block PI3K, polarized epithelial cells were incubated with either 20 µM wortmannin (Calbiochem) for 30 minutes or with 10 µM LY294002 (Cell Signal) for 1 hour prior to bacterial infection. Experiments were repeated three times.
Results:

The effect on epithelial integrity of activating the TLR2/PI3K pathway by curli amyloid fibrils. Epithelial permeability was measured by applying FITC-dextran to the apical compartment of the polarized T-84 cells 24 hours after the infection with either wild type *S. Typhimurium* or the csgBA mutant. Two hours following FITC-dextran application, fluorescence was determined in the basolateral compartment. CsgBA mutant-infected wells exhibited an increased fluorescence compared to the wells infected with the wild type *S. Typhimurium* (FIG. 2A). To see if the increased fluorescence observed in the basolateral compartments of csgBA mutant-infected wells indeed corresponded with a disruption in the epithelial membrane, the transepithelial electrical resistance (TER) across the permeable tissue culture insert was determined prior to the infection as well as 24 hours post-infection. A percent change in TER was then determined. TER was significantly reduced when the polarized cells were infected with the csgBA mutant as compared to the wild type *S. Typhimurium* at 24 h post-infection (FIG. 2B).

Figure 2C:
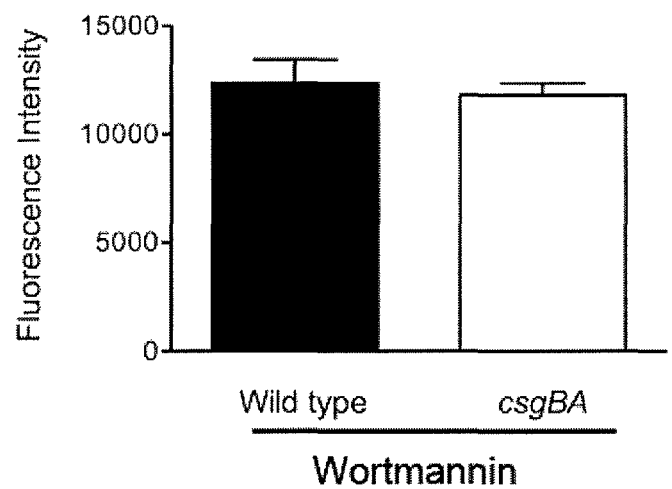
FIG. 2C illustrates the treatment of T-84 cells with the specific PI3K inhibitor Wortmannin (20 µM) for 30 minutes.
Figure 2D:
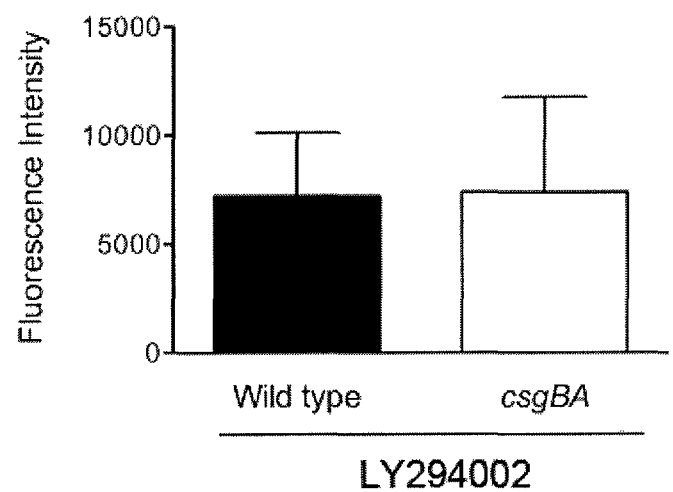
FIG. 2D illustrates the treatment of T-84 cells with the specific PI3K inhibitor LY294002 for 1 hour (10 µM).

The PI3K inhibitors LY294002 and Wortmannin are often used to block PI3K activity (Walker E H et al, 2000. Structural determinants of phosphoinositide 3-kinase inhibition by wortmannin, LY294002, quercetin, myricetin, and staurosporine. *Mol Cell* 6:909-919). To determine if the csgBA-dependent increase in epithelial permeability was due to an activation of TLR2/PI3K pathway, the polarized epithelial cells were pretreated with the irreversible PI3K inhibitors, Wortmannin or LY294002. Treatment with either inhibitor abolished the epithelial permeability difference observed between infection with the wild type *S. Typhimurium* and the csgBA mutant (FIG. 2C-D). Similar experiments using polarized Caco-2 cells also yielded similar results showing that activation of TLR2/PI3K pathway with curli fibrils maintains epithelial integrity. (data not shown)

Figure 3:
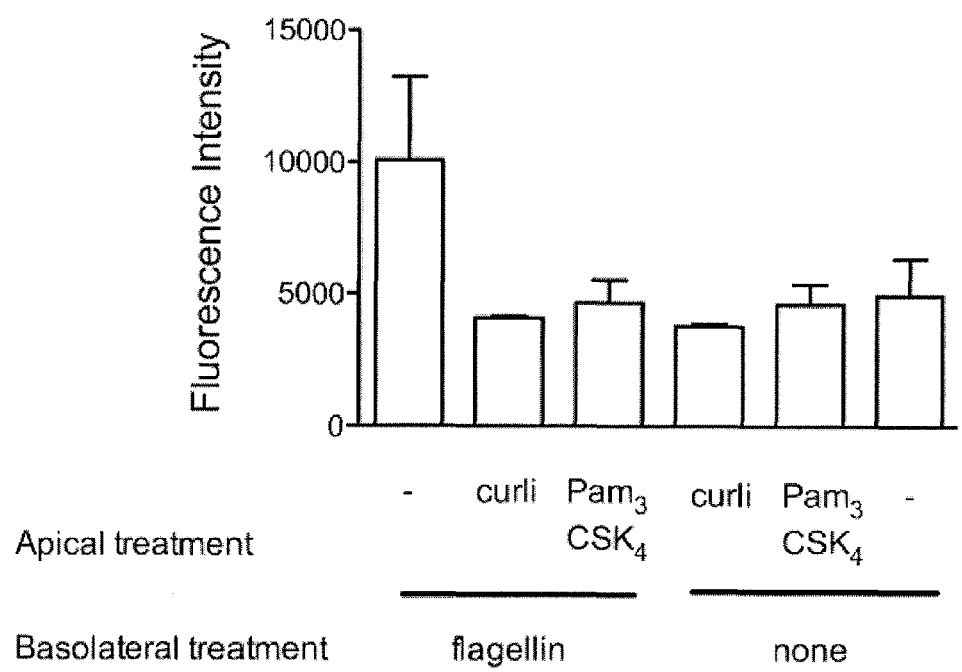
FIG. 3 illustrates the treatment of polarized T-84 cells with either flagellin (0.01 µg/ml) in the basolateral chamber or phosphate buffered saline (PBS). Simultaneously, either curli fibrils (10 µg/ml) or synthetic TLR2 ligand, Pam$_3$CSK$_4$ (0.1 µg/ml) were added to the apical chamber. Epithelial permeability was determined by using FITC dextran after 24 hours to the apical chamber for 2 hours. Fluorescence was determined in the basolateral supernatants using a BMG Omega plate reader.

Flagellin, the major protein subunit of flagella, is a conserved surface structure of bacteria that activates TLR5 expressed basolaterally in the epithelium. To simulate the effects on epithelial integrity of activating TLR2 and TLR5 by bacterial components during invasion, polarized T-84 cells were stimulated basolaterally with flagellin and/or apically with curli fibrils or $Pam_3CSK_4$ and the epithelial permeability was measured by applying FITC-Dextran in the apical chamber. While basolateral addition of flagellin to polarized epithelia resulted in an increase in the epithelial permeability as measured by increased fluorescence in the basolateral chamber, addition of purified curli amyloid fibrils or $Pam_3CSK_4$ did not affect the permeability. However, simultaneous addition of flagellin to the basolateral chamber and curli amyloid fibrils or the synthetic TLR2/1 ligand, $Pam_3CSK_4$ to the apical chamber helped to restore the epithelial permeability to the levels of untreated epithelia (FIG. 3).

Overall, these results indicate that the detection of curli amyloid fibrils help polarized epithelia to maintain the epithelial barrier integrity via TLR2/PI3K activation.

Example 4

Activation of TLR2 by Curli Fibrils In Vivo Decreases Epithelial Permeability and Reduces Bacterial Translocation The following experiments demonstrate that activation of TLR2 by curli fibrils in mice infected with wild type *S. Typhimurium* decreases epithelial permeability and reduces bacterial translocation.
Mice Experiments Six- to eight-week old female C57BL/6 mice were obtained from Jackson Laboratory. TLR2-deficient mice (B6.129-TLR2$^{tm1Kir}$/J) were purchased from Jackson Laboratory and were maintained and bred in a germ-free animal facility.

The use of FITC-dextran to assess intestinal permeability in vivo has been previously described. Briefly, groups of 3-4 mice were orally inoculated with either $1 \times 10^9$ bacteria (wild type *S. Typhimurium* or csgBA mutant) in LB or mock-infected with sterile LB. 72 hours post-infection, 150 µl of 80 mg/ml FITC-dextran was administered orally. Mice were sacrificed 4 hours later and blood was collected via cardiac puncture. Blood was collected into microcentrifuge tubes coated with a mixture of anticoagulant heparin (15 mg/ml) and acid citrate dextrose (20 mM citric acid, 100 mM sodium citrate, 5 mM dextrose) (Alteri C J et al., 2007. *Mycobacterium tuberculosis* produces pili during human infection. *Proc Natl Acad Sci USA* 104:5154-5150). Blood was then spun at 1000 rpm for 20 minutes to separate serum from whole blood cells. Fluorescence intensity in the serum was then determined using the Omega Plate Reader at 485 nm excitation and 520 nm emission (BMG Labtech).

Figure 4A:
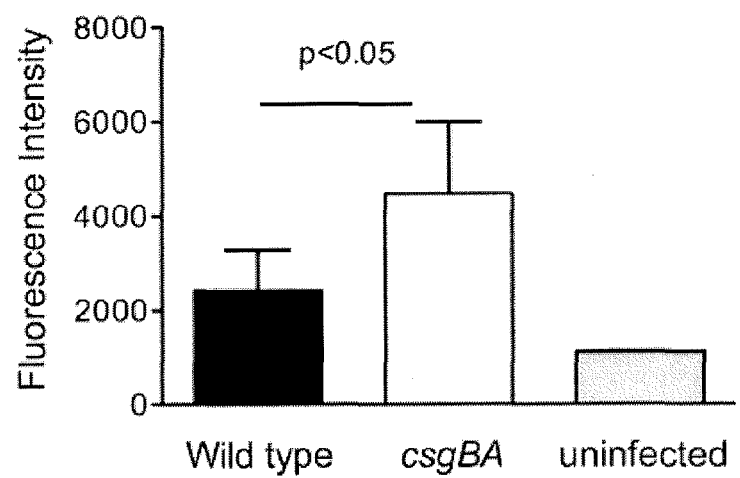
FIG. 4A illustrates the intragastric infection of C57BL/6 mice with 1×10$^9$ CFU wild-type *S. Typhimurium*, isogenic csgBA mutant or mock (LB) for 72 hours. 150 µl of 80 mg/ml FITC-dextran was administered intragastrically 4 hours prior to sacrifice of the animals. Blood was collected and fluorescence was measured in the serum using a BMG Omega plate reader. Significant statistical differences are indicated (P<0.05).
Figure 4B:
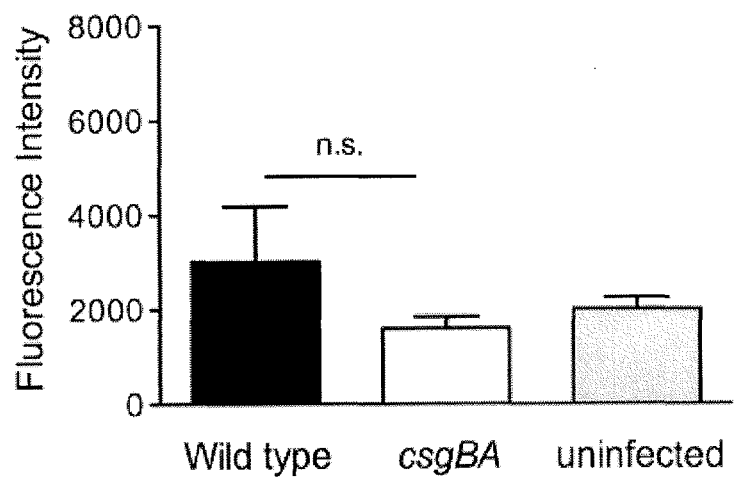
FIG. 4B illustrates the infection of TLR2-deficient mice under the same conditions as in FIG. 4A.

To assess bacterial numbers, oral inoculation of bacteria as described above was performed. Mice were sacrificed 72 hours later and tissue samples from the cecum, liver, spleen, mesenteric lymph nodes and Peyer's Patches were collected. Colonic content was collected in 1 ml of sterile PBS. Organ samples were homogenized in sterile PBS and appropriate serial dilutions were plated on LB-nalidixic acid agar plates. All the animal experiments were repeated three times.
Results:

To determine whether curli fibrils are an important modulator of TLR2-mediated epithelial barrier integrity generated by bacteria in vivo, C57BL/6 mice were intragastrically infected with wild type *S. Typhimurium* or the csgBA mutant. 72 hours post-infection, 150 µl of 80 mg/ml FITC-dextran was administered intragastrically. Four hours post-FITC-dextran administration, fluorescence was quantified in serum. Consistent with the in vitro data, serum from mice infected with the csgBA mutant exhibited higher levels of fluorescence compared to the serum of mice infected with the wild type *S. Typhimurium* (FIG. 4A). When the same experiment was repeated using TLR2-deficient mice, no significant changes were observed in the fluorescence levels in the sera of mice infected with wild type *S. Typhimurium* and the fluorescence levels in the sera of mice infected with the csgBA mutant (FIG. 4B).

Figure 5A:
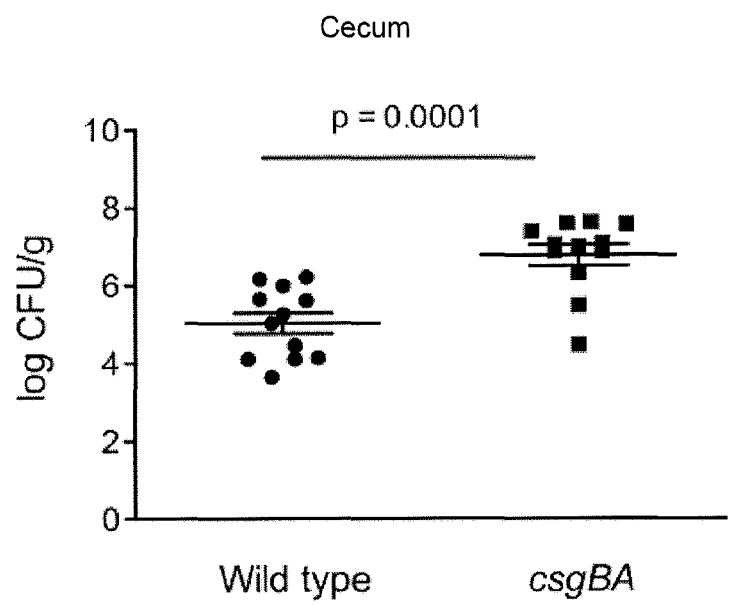
FIG. 5A illustrates the intragastric infection of C57BL/6 mice with 1×10$^9$ CFU wild-type *S. Typhimurium*, isogenic csgBA mutant or mock infected (LB) for 72 hours. Bacterial count was determined in the cecal tissue by plating serial dilutions on media.
Figure 5B:
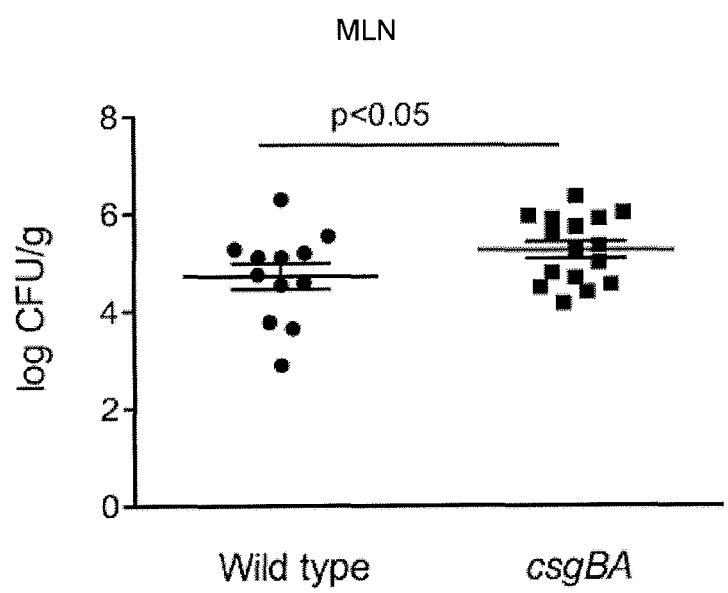
FIG. 5B illustrates the determination of bacterial count in the mesenteric lymph nodes under the same conditions as in FIG. 5A.
Figure 5C:
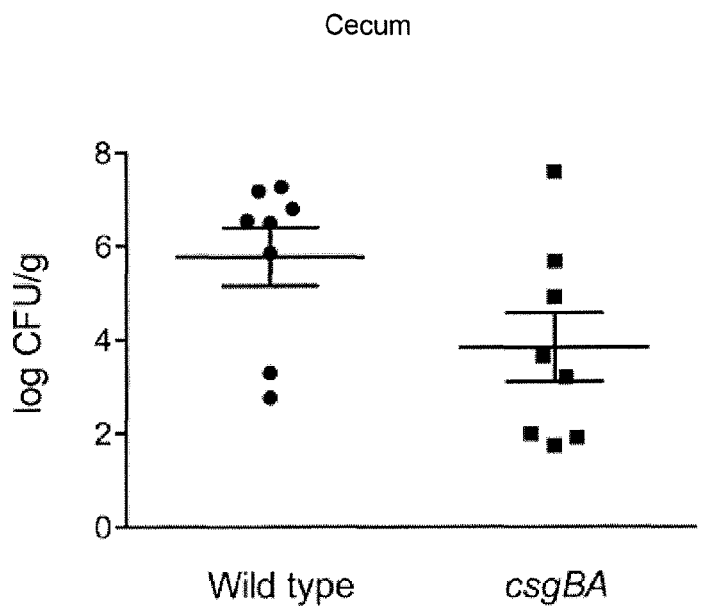
FIG. 5C illustrates the determination of bacterial count in cecal tissue of TLR2-deficient animals under the same conditions as in FIG. 5A.
Figure 5D:
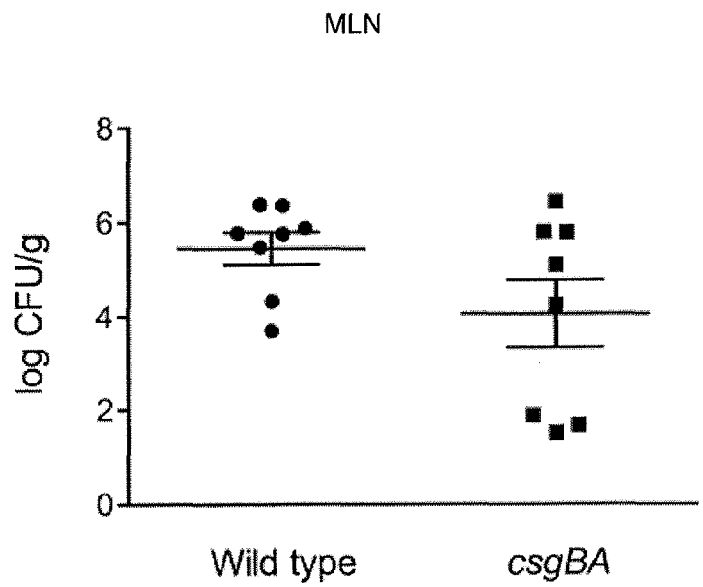
FIG. 5D illustrates the determination of bacterial count in mesenteric lymph nodes of TLR2-deficient animals under the same conditions as in FIG. 5A.
Figure 6A:
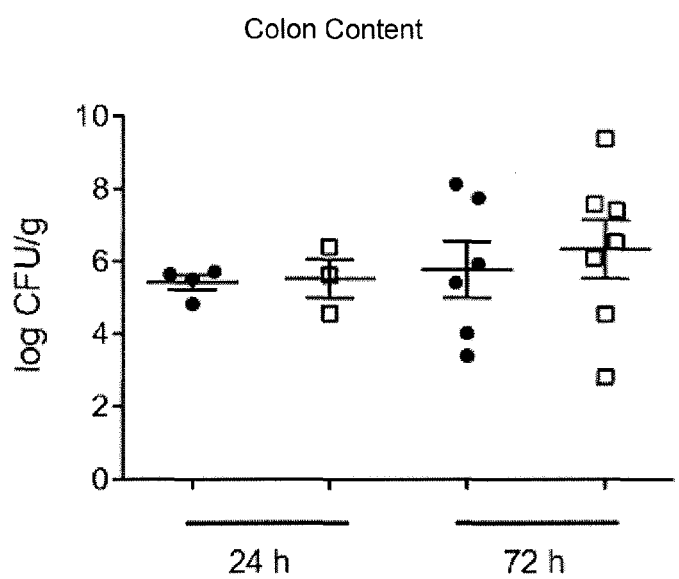
FIG. 6A illustrates the determination of bacterial count in the colonic contents of C57BL/6 mice infected with 1×10$^9$ CFU wild-type *S. Typhimurium* (circles) or its isogenic csgBA mutant (squares) for 24 and 72 hours.
Figure 6B:
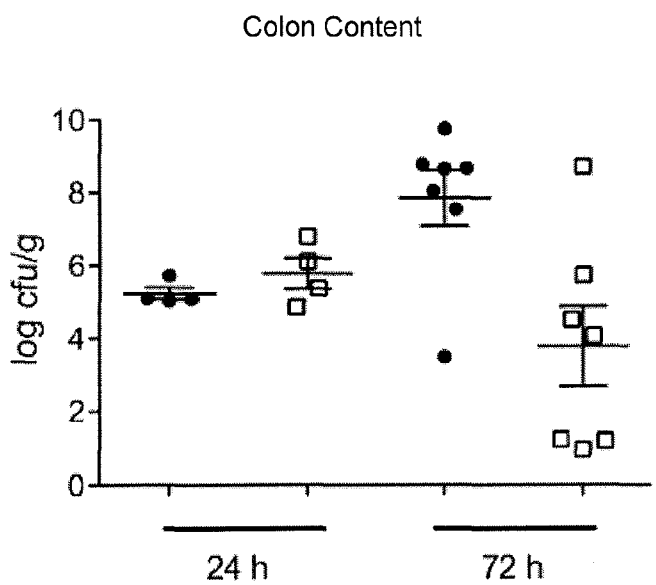
FIG. 6B illustrates the determination of bacterial count in the colonic contents of TLR2-deficient mice under the same conditions as in FIG. 6A.

The bacterial numbers were determined in cecal tissue and mesenteric lymph nodes of infected mice. Significantly higher bacterial numbers were recovered from the cecum and mesenteric lymph nodes of C57BL/6 mice compared to the mice infected with wild type *S. Typhimurium* (FIGS. 5A and 5B). In TLR2-deficient mice however, lower numbers of the csgBA mutant strain were recovered from the cecal tissue and the mesenteric lymph nodes compared to the wild type *S. Typhimurium* (FIGS. 5C and 5D). To ensure that the mice were equally infected, bacteria were enumerated in the colon contents of mice 24 and 72 hours post-infection. 24 hours post-infection, there were no significant differences between the numbers of wild type *S. Typhimurium* and the csgBA mutant in infected C57BL/6 mice or TLR2-deficient mice. However, at 72 hours the wild type *S. Typhimurium* bacterial numbers in colon contents of TLR2-deficient mice increased 2 logs over the bacterial numbers at 24 hours. This suggests that TLR2 plays a role in controlling bacterial infection with wild type *S. Typhimurium*. Interestingly, TLR2-deficient mice infected with the csgBA mutant had much lower bacterial numbers in the colon contents compared to the mice infected with the wild type *S. Typhimurium* at 72 hours (FIGS. 6A and 6B).

Overall, these results suggest that the activation of TLR2 by curli amyloid fibrils in the wild type *S. Typhimurium* infected mice promoted the maintenance of the intestinal epithelial barrier whereas mice infected with the csgBA mutant exhibited a more permeable epithelium as seen with the increased translocation of the csgBA mutant into the cecal tissue and the mesenteric lymph nodes.

Example 5

Curli Fibers Induce IL-10 Production

Figure 7A:
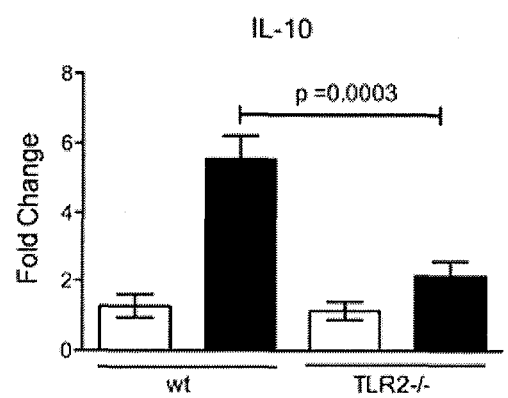
FIG. 7A illustrates the induction of IL-10 production in the colon after intraperitoneal injection of purified *Salmonella* curli fibers.
Figure 7B:
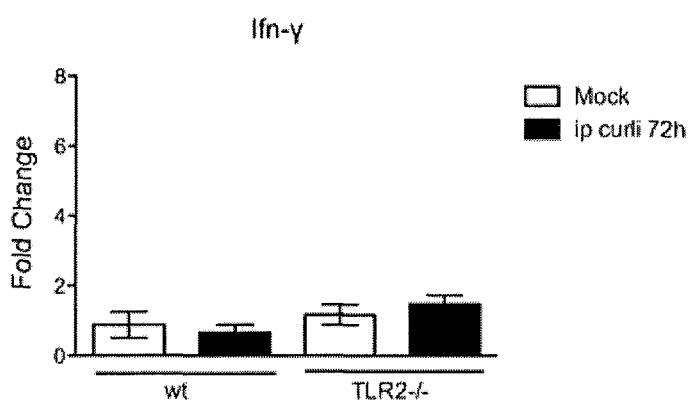
FIG. 7B illustrates the lack of induction of IFN-gamma production in the colon after intraperitoneal injection of purified *Salmonella* curli fibers.
Figure 7C:
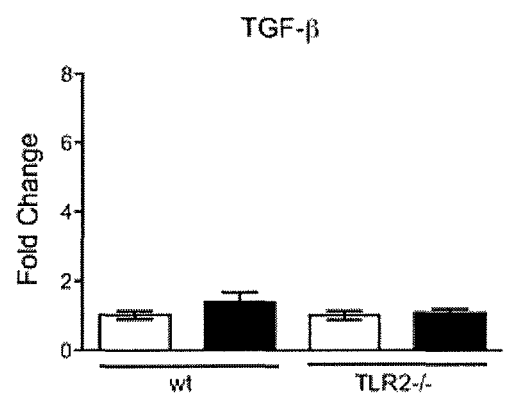
FIG. 7C illustrates the lack of induction of TGF-beta production in the colon after intraperitoneal injection of purified *Salmonella* curli fibers.

The following experiments demonstrate that curli fibers induce the production of the immunomodulatory cytokine IL-10.
Mice Experiments Six- to eight-week old female C57BL/6 mice and TLR2-deficient mice (B6.129-TLR2$^{tm1Kir}$/J) were injected with purified curli fibrils (5 mg/kg) intraperitoneally. 72 hours after injection, IL-10, TGF-beta, IFN-gamma expression in the intestine. Only IL-10 was upregulated at this time point and its expression was dependent on TLR2 (FIG. 7A-C).

Figure 8:
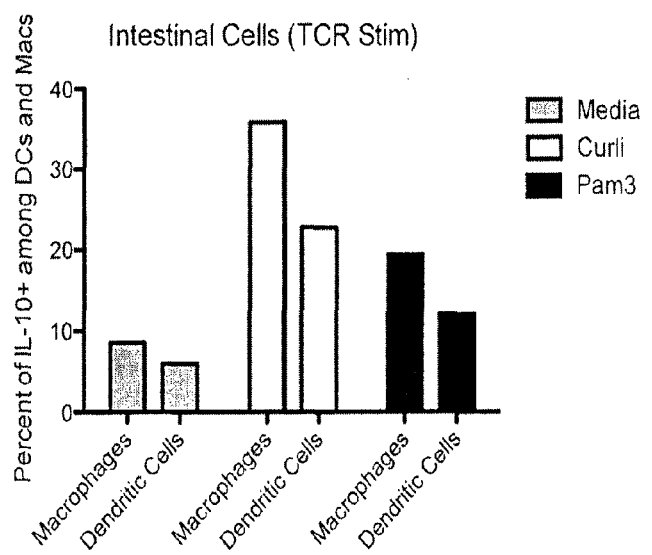
FIG. 8 illustrates the induction of IL-10 production in dendritic cells and macrophages after intraperitoneal injection of purified *Salmonella* curli fibers.
Figure 9A:
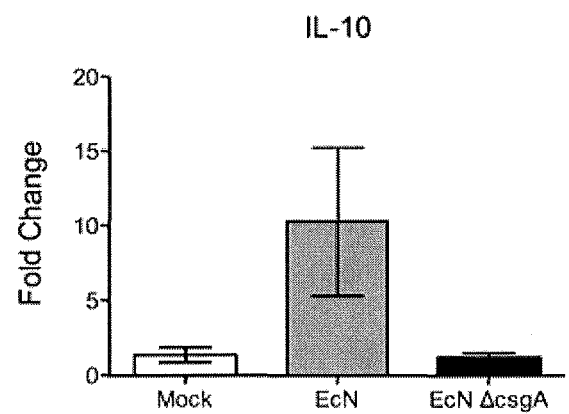
FIG. 9A illustrates the induction of IL-10 production in the colon after oral injection of Nissle (EcN) and its curli mutant (EcN ΔcsgA) to mice.
Figure 9B:
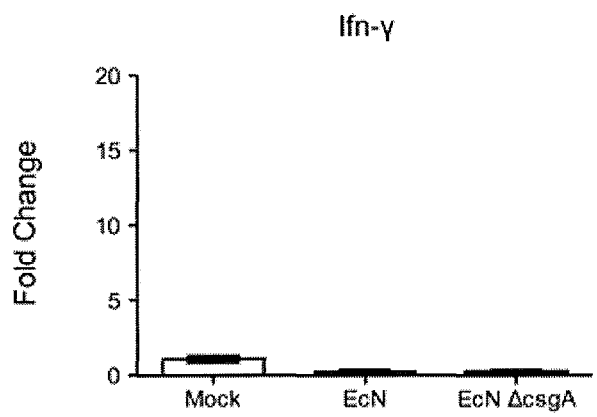
FIG. 9B illustrates the lack of induction of IFN-gamma production in the colon after oral injection of Nissle (EcN) and its curli mutant (EcN ΔcsgA) to mice.
Figure 9C:
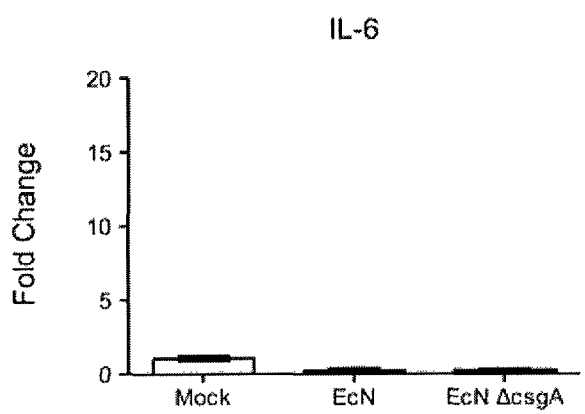
FIG. 9C illustrates the induction of IL-6 production in the colon after oral injection of Nissle (EcN) and its curli mutant (EcN ΔcsgA) to mice.
Figure 9D:
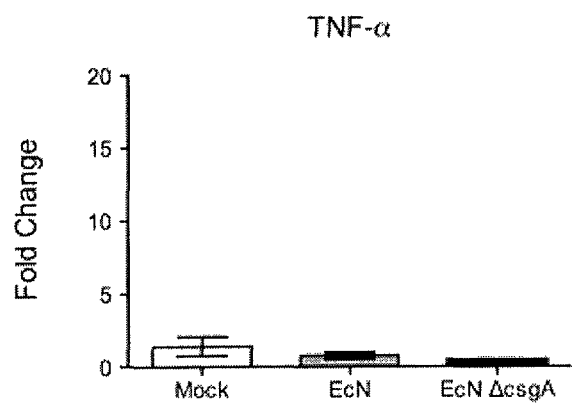
FIG. 9D illustrates the induction of TNF-alpha production in the colon after oral injection of Nissle (EcN) and its curli mutant (EcN ΔcsgA) to mice.

Interestingly, IL-10 was specific to the intestine because no expression was observed in the spleen. When intestinal cells were purified and stimulated ex-vivo with curli it caused production of IL-10 by 48 hours that was dependent on TLR2 (data not shown). When the cell population was investigated by flow cytometry, DCs and macrophages were found to produce large amounts of IL-10 (FIG. 8).

Next, since curli fibrils are expressed by commensal *E. coli* strains we inoculated mice with a wild type probiotic *E. coli* strain that expresses curli or its csgA mutant (curli-). 48 hours after wild type *E. coli* had a significant increase in IL-10 expression compared to mice inoculated with the curli mutant (FIG. 9A-D). Consistent with these findings, treatment of bone marrow derived macrophages with Nissle curli resulted in high levels of IL-10 compared to TLR2 deficient macrophages.

Figure 10A:
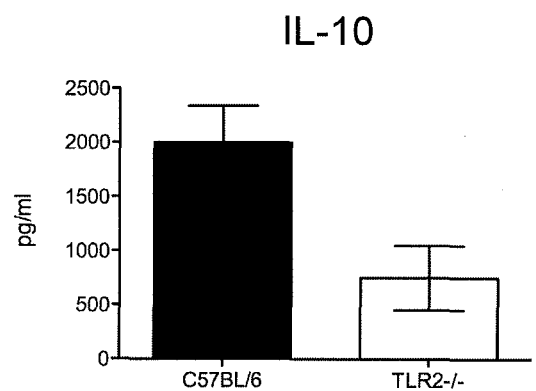
FIG. 10A illustrates the induction of IL-10 production in bone marrow-derived macrophages in a TLR2-dependant manner by *E. coli* Nissle curli fibers.
Figure 10B:
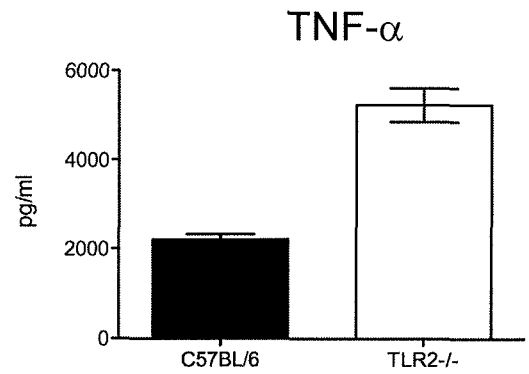
FIG. 10B illustrates that TNF-alpha is not induced under similar conditions.
Figure 10C:
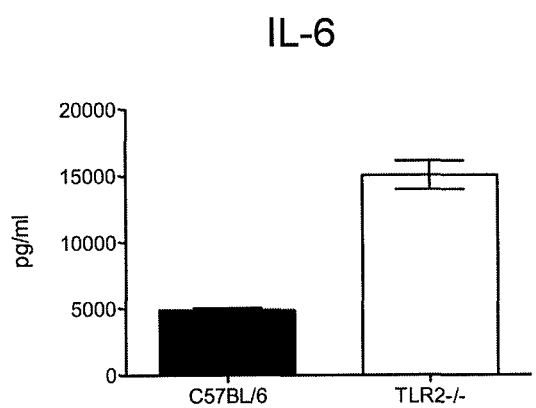
FIG. 10C illustrates that IL-6 is not induced under similar conditions.

Conversely, TLR2 deficient macrophages treated with curli showed lower levels of IL-10 and higher levels of IL-6 and TNF-alpha production compared to wild type macrophages suggesting that curli-induced IL-10 production suppresses the IL-6 and TNF-alpha production in a TLR2 dependent manner (FIG. 10A-C).

Thus, in addition to the direct effects of curli in the epithelial barrier, it also exerts beneficial effects on the intestinal epithelium through production of the immunomodulatory cytokine IL-10.

Example 6

Curli and eDNA are Found Tightly Associated in *Salmonella* Biofilms

Figure 11A:
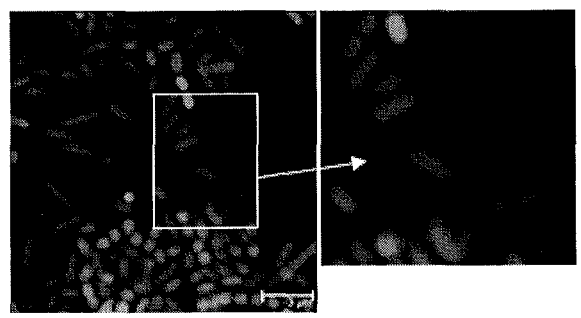
FIG. 11A and FIG. 11B illustrate that DNA is found associated with curli fibers in *Salmonella* biofilms. *S. Typhimurium* static biofilms were stained with propidium iodide to monitor DNA release (dark grey). *S. Typhimurium* (light grey) carries a plasmid containing a GFP reporter system where GFP is fused to the csgBA promoter.
Figure 11B:
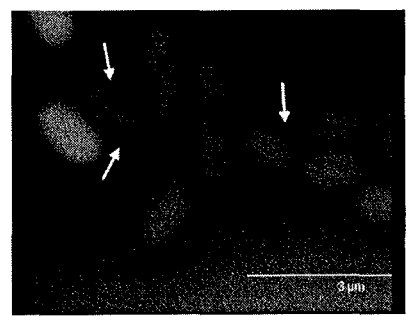

The following experiments demonstrate that curli fibers and extracellular DNA are tightly associated in *S. Typhimurium* biofilms.
Confocal Microscopy We investigated the presence of DNA in *S. Typhimurium* biofilms by fluorescent confocal microscopy. We observed significant cell death and DNA release by 72 hours in *S. Typhimurium* static biofilms grown in LB broth lacking salt at 30° C. (FIG. 11A). Interestingly, DNA localized around the cells that express curli as demonstrated by a GFP reporter system where GFP was fused to the csgBA promoter (FIG. 11B).

Curli fibers were purified from *S. Typhimurium* biofilm according to the following protocol. *S. Typhimurium* biofilm was disrupted and cells were lysed by sonication followed by enzymatic digestion (RNase, DNase, lysozyme) and 1% SDS treatment. Preparations were then subjected to boiling in SDS loading buffer several times, followed by preparative sodium dodecyl sulphate-polyacrylamide gel electrophoresis (SDS-PAGE). Insoluble materials (curli fibrils) retained in the well of the SDS-PAGE gel were collected after the electrophoresis.

Figure 11C:
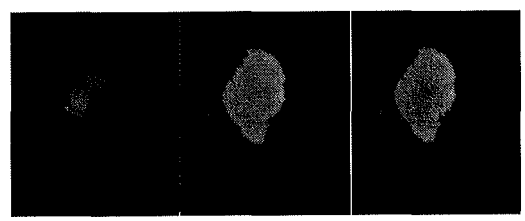
FIG. 11C illustrates that DNA is found associated with curli fibers in *Salmonella* biofilms. Purified curli fibers were stained with Thioflavin T, an amyloid-specific stain (left) and DAPI, a nucleic acid stain (middle). Colocalization of the stains was observed (right).

Interestingly, when curli preparations were stained with Thioflavin T, an amyloid-specific stain, and DAPI, a nucleic acid stain, co-localization of both stains occurred, suggesting that the purified curli fibers contained nucleic acids (FIG. 11C). Furthermore, this data indicated that nucleic acids associated with curli fibers were resistant to DNase and RNase treatment.

Example 7

DNA Accelerates the Polymerization of Curli Fibers

The following experiments demonstrate that DNA accelerates the polymerization of curli fibers.

Figure 12A:
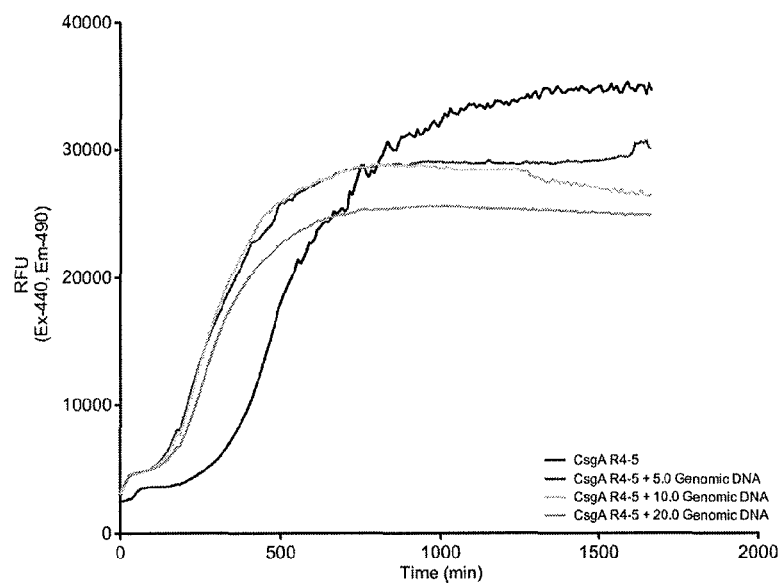
FIG. 12A illustrates that genomic *Salmonella* DNA accelerates the polymerization of synthetic curli peptide CsgAR4-5.
Figure 12B:
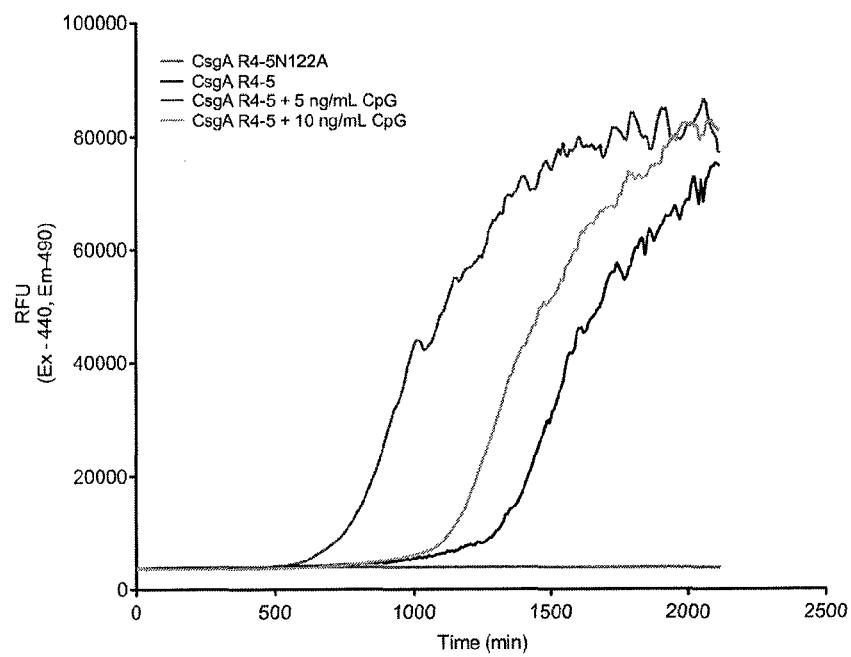
FIG. 12B illustrates that CpG oligonucleotides accelerate the polymerization of synthetic curli peptide CsgAR4-5.

Utilizing a synthetic peptide made from the primary amino acid sequence of the fourth and fifth repeats of the CsgA monomer of curli (CsgAR4-5: SDI TVG QYG GNN AAL VNQ TAS DSS VMV RQV GFG NNA PAN QY (SEQ ID NO: 9)), we performed in vitro polymerization assays in the presence or absence of increasing concentrations of (a) a DNA sequence that is high in CpG: 5'-tccatgacgttcctgacgtt-3' (SEQ ID NO: 3), (b) a synthetic nucleic acid sequence used as a TLR9 agonist: 5'-tccatgacgttcctgacgtt-3' (SEQ ID NO: 4), and (c) genomic DNA purified from *Salmonella*. Thioflavin T was used to measure the polymerization in the presence of DNA. DNA from all three sources was able to accelerate the polymerization of CsgAR4-5 by decreasing the time spent in the lag phase of polymerization (FIG. 12A-B).

Figure 13A:
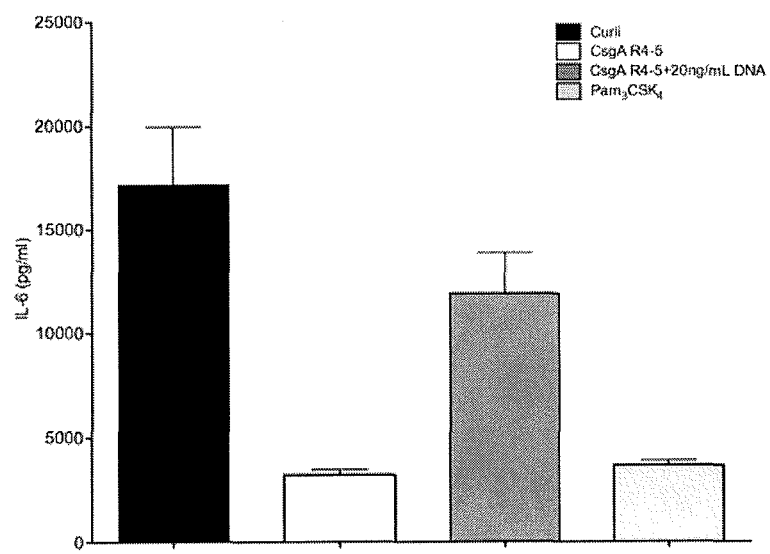
FIG. 13A illustrates that synthetic curli peptide CsgAR4-5 containing genomic DNA induces higher levels of IL-6 in bone marrow-derived macrophages.
Figure 13B:
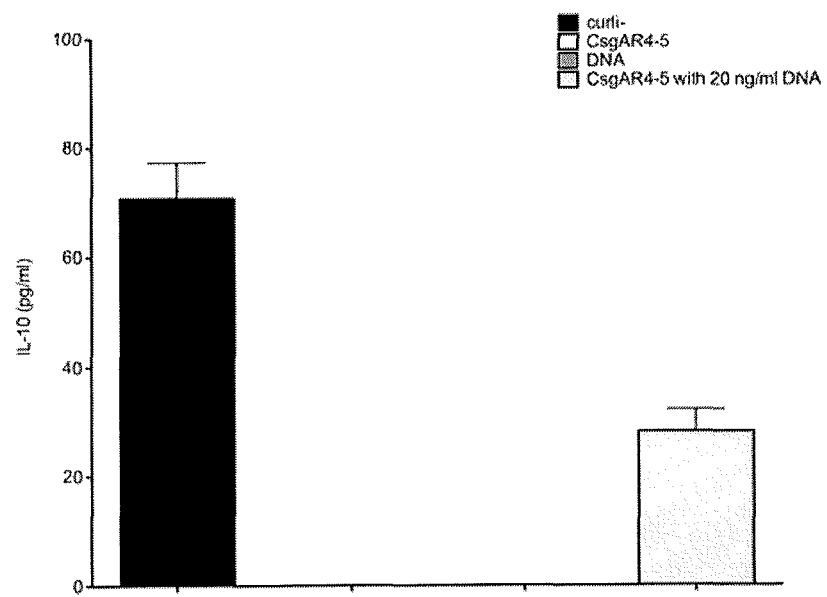
FIG. 13B illustrates that synthetic curli peptide CsgAR4-5 containing genomic DNA induces higher levels of IL-10 in bone marrow-derived macrophages.

When we tested synthetic peptide alone or complexed with external DNA (eDNA), we found that CsgAR4-5 (curli)/eDNA complex induced higher levels of IL-10 in bone marrow-derived dendritic cells compared to CsgAR4-5 or eDNA alone. Given the knowledge that amyloids are recognized through TLR2/1 and bacterial DNA is recognized through TLR9, our data suggests that amyloid/DNA complexes may exert immunomodulatory effects on the immune system through TLR2/TLR1 and TLR9 (FIG. 13A-B).

All references herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should also be made to the appended claims, rather than to the foregoing specification, as indicating the scope of the invention.

The invention claimed is:

1. A method for the treatment of a subject having inflammatory bowel disease or oral ulcers comprising the step of administering to the subject an effective amount of a composition comprising:
   (a) an isolated curli fibril comprising a naturally occurring CsgA polypeptide, a naturally occurring CsgB polypeptide, or a combination of a naturally occurring CsgA polypeptide and a naturally occurring CsgB polypeptide; or
   (b) an isolated curli fibril having epithelium peimeability-reducing activity comprising:
      (i) a CsgA polypeptide variant which differs from a naturally occurring CsgA polypeptide in that from 1 to 5 amino acids have been substituted, deleted or added;
      (ii) a CsgB polypeptide variant which differs from a naturally occurring CsgB polypeptide in that from 1 to 5 amino acids have been substituted, deleted or added; or
      (iii) a combination of said CsgA polypeptide variant and said CsgB polypeptide variant.

2. The method of claim 1 wherein said composition is membrane-free.

3. The method of claim 1 wherein said isolated curli fibril comprises a naturally occurring CsgA polypeptide.

4. The method of claim 1 wherein the subject has inflammatory bowel disease.

5. The method of claim 4 wherein said inflammatory bowel disease is Crohn's disease or ulcerative colitis.

6. The method of claim 1 wherein the composition is administered orally, intracolonically or topically.

7. The method of claim 1 wherein the subject is a mammal.

8. The method of claim 7 wherein the subject is a human.

9. A method for decreasing permeability of epithelium of the small intestine or large intestine in a subject in need thereof comprising the step of administering to the subject an effective amount of a composition comprising:
   (a) an isolated curli fibril comprising a naturally occurring CsgA polypeptide, a naturally occurring CsgB polypeptide, or a combination of a naturally occurring CsgA polypeptide and a naturally occurring CsgB polypeptide; or
   (b) an isolated curli fibril having epithelium permeability-reducing activity comprising:
      (i) a CsgA polypeptide variant which differs from a naturally occurring CsgA polypeptide in that from 1 to 5 amino acids have been substituted, deleted or added;
      (ii) a CsgB polypeptide variant which differs from a naturally occurring CsgB polypeptide in that from 1 to 5 amino acids have been substituted, deleted or added; or
      (iii) a combination of said CsgA polypeptide variant and said CsgB polypeptide variant.

10. The method of claim 9 wherein said composition is membrane-free.

11. The method of claim 9 wherein said isolated curli fibril comprises a naturally occurring CsgA polypeptide.

12. The method of claim 9 wherein the subject has inflammatory bowel disease.

13. The method of claim 12 wherein said inflammatory bowel disease is Crohn's disease or ulcerative colitis.

14. The method of claim 9 wherein the composition is administered orally, intracolonically or topically.

15. The method of claim 9 wherein the subject is a mammal.

16. The method of claim 15 wherein the subject is a human.

* * * * *

UNITED STATES PATENT AND TRADEMARK OFFICE
CERTIFICATE OF CORRECTION

PATENT NO. : 9,814,756 B2
APPLICATION NO. : 14/407568
DATED : November 14, 2017
INVENTOR(S) : Cagla Tukel Page 1 of 1

It is certified that error appears in the above-identified patent and that said Letters Patent is hereby corrected as shown below:

In the Specification

In Column 1, under the "Reference to Government Grant", please replace the text on Lines 16-18 with the following:
-- The invention was made with government support under grant no. AI057168 awarded by the National Institutes of Health. The government has certain rights in this invention. --

Signed and Sealed this
Twenty-eighth Day of November, 2023

Katherine Kelly Vidal
*Director of the United States Patent and Trademark Office*